US009394269B2

(12) United States Patent
Rinsch et al.

(10) Patent No.: US 9,394,269 B2
(45) Date of Patent: Jul. 19, 2016

(54) PROCESS-SCALE SYNTHESIS OF UROLITHINS

(71) Applicant: Amazentis SA, Ecublens (CH)

(72) Inventors: Christopher L. Rinsch, Morges (CH); Roland Müller, Regensburg (DE); Wolfgang Skranc, Vienna (AT)

(73) Assignee: Amazentis SA, Ecublens (CH)

( * ) Notice: Subject to any disclaimer, the term of this patent is extended or adjusted under 35 U.S.C. 154(b) by 0 days.

(21) Appl. No.: 14/578,870

(22) Filed: Dec. 22, 2014

(65) Prior Publication Data

US 2015/0183758 A1 Jul. 2, 2015

Related U.S. Application Data

(60) Provisional application No. 61/919,923, filed on Dec. 23, 2013.

(51) Int. Cl.
*A61K 31/366* (2006.01)
*C07D 311/80* (2006.01)
*A61K 33/34* (2006.01)

(52) U.S. Cl.
CPC ............ *C07D 311/80* (2013.01); *A61K 31/366* (2013.01); *A61K 33/34* (2013.01)

(58) Field of Classification Search
CPC ............................ C07D 311/80; A61K 31/366
See application file for complete search history.

(56) References Cited

U.S. PATENT DOCUMENTS

| 2002/0193596 A1 | 12/2002 | Sebti et al. |
| 2004/0144954 A1 | 7/2004 | Wellinghoff et al. |
| 2008/0031862 A1 | 2/2008 | Ghosal |

FOREIGN PATENT DOCUMENTS

| EP | 2674422 A1 | 12/2013 | |
| WO | WO-2004/050651 A1 | 6/2004 | |
| WO | WO-2006/046071 A1 | 5/2006 | |
| WO | WO-2008/016554 A1 | 2/2008 | |
| WO | WO-2011/051225 A1 | 5/2011 | |
| WO | WO 2012/108455 | * 8/2012 | ........... C07D 311/80 |

OTHER PUBLICATIONS

Hassan, J. et al., "Aryl-Aryl Bond Formation One Century after the Discovery of the Ullmann Reaction", *Chem. Rev.*, 102:1359-1469 (American Chemical Society, USA, 2002).
Kraatz, U. et al., "Zur Synthese von Phenanthridinonen-(6) aus 3,4 disubstituierten Cumarinen und ihre Reaktion mit Methylmagnesiumjodid zu Phenanthridiniumjodiden", *Chemische Berichte*, 106(1):62-68 (University of Bonn, Germany, Jan. 1, 1973).
Krzeszewski, M. et al., "Color-Tunable Fluorescent Dyes Based on Benzo[c]coumarin", *European Journal of Organic Chemistry*, 2013(25):5631-5644 (Wiley-Verlag GmbH & Co. KGaA, Weinheim, Sep. 16, 2013).
Kudo, K. et al., "Scalable Synthesis of 8-Amino-3-hydroxy-6*H*-benzo[c]chromen-6-one: Key Intermediate for SEGRA via the Hurtley Reaction", *Organic Process Research & Development*, 19(1):309-314 (American Chemical Society, Dec. 11, 2014).
Pandey, J. et al., "Synthesis and biological activities of some new dibenzopyranones and dibenzopyrans: search for potential oestrogen receptor agonists and antagonists", *Bioorganic and Medicinal Chemistry*, 12(9):2239-2249 (Elsevier Ltd., Jan. 1, 2004).
Sun, W. et al., "6*H*-Benzo[c]chromen-6-one derivatives as selective ERβ agonists", *Bioorganic and Medicinal Chemistry Letters*, 16(6):1468-1472 (Elsevier Ltd., Jan. 18, 2006).
Partial International Search Report from PCT/US2014/071824 dated Mar. 18, 2015.
Bialonska, D. et al., "Urolithins, Intestinal Microbial Metabolites of Pomegranate Ellagitannins, Exhibit Potent Antioxidant Activity in a Cell-Based Assay", *J. Agric. Food Chem.*, 57:10181-10186 (American Chemical Society, USA, 2009).
Boulangé, A. et al., "Diastereoselective IBX Oxidative Dearomatization of Phenols by Remote Induction: Towards the Epicocconone Core Network", *Chem. Eur.*, 17:10241-10245 (Wiley-VCH Verlag GmbH & Co, KGaA, Weinheim, Germany, 2011).
Cozza, G. et al., "Urolithin as a Converging Scaffold Linking Ellagic Acid and Coumarin Analogues: Design of Potent Protein Kinase CK2 Inhibitors", *Chem. Med. Chem.*, 6:2273-2286 (Wiley-VCH Verlag GmbH & Co. KGaA, Weinheim, Germany, 2011).
Devlin, J. P., "6*H*-dibenzo[b,d]pyrans. I. Synthesis", *Can. J. Chem.*, 53:343-349 (Pharma Research Canada, Ltd., Point Claire, QC, 1975).
Garazd, Y. L. et al., "Modified Coumarins. 15. Condensed Psoralen Derivatives Based on Substituted Dibenzo[b,d]pyran-6-ones", *Chemistry of Natural Compounds*, 40(6):535-540 (Springer Science+Business Media, Inc., 2004).
Garazd, Y. L. et al., "Synthesis of substituted benzo[c]furo[3,2-g]chromen-5-ones", *Ukrainica Bioorganica Acta* 1-2:49-55 (2004).
Ghosal, S. et al., "Shilajit. Part 4. Chemistry of Two Bioactive Benzopyrone Metabolites", *J. Chem. Research (S)*, 11:350-351 (1989).
Henderson, G. B. et al., "Synthesis of Chlorinated Isocoumarin Derivatives", *J. Chem. Soc. Perkin Trans.*, 1:1111-1115 (1982).
Ito, H. et al., "Identification of Urinary and Intestinal Bacterial Metabolites of Ellagitannin Geraniin in Rats", *J. Agric. Food Chem.*, 56(2):393-400 (American Chemical Society, USA, 2008).
Lederer, E. et al., Synthèse de la dihydroxy-4.4' dibenzo-α pyrone, pigment des glandes à parfum du Castor (Castor fiber); *Bull. Soc. Chim. France*, 5(15:831-834 (1948).
Nishide, K. et al., "Development of Odorless Thiols and Sulfides and Their Applications to Organic Synthesis", *Monatshefte für Chemie (Chemical Monthly)*, 135(2):138-200 (Austria, 2004).

(Continued)

*Primary Examiner* — Erich A Leeser

(74) *Attorney, Agent, or Firm* — Dana M. Gordon; Foley Hoag LLP

(57) ABSTRACT

Disclosed is a method of preparing a urolithin, or an intermediate or analog thereof, having a dibenzo[b,d]pyran-6-one core. The method is especially advantageous for the large-scale preparation of urolithins or intermediates or analogs thereof. The method may optionally include the preparation of a urolithin, or an intermediate or analog thereof, as a pharmaceutically acceptable salt.

16 Claims, 2 Drawing Sheets

(56) References Cited

OTHER PUBLICATIONS

Node, M. et al., "Odorless substitutes for foul-smelling thiols: syntheses and applications", *Tetrahedron Letters*, 42(52):9207-9210 (Elsevier Science Ltd., 2001).

Rose N. R. et al., "Inhibitor Scaffolds for 2-Oxoglutarate-Dependent Histone Lysine Demethylases", *J. Med. Chem.*, 51(22):7053-7056 (American Chemical Society, USA, 2008).

Saeed, A., "Synthesis of (±)-6-O-methyl and 7-demethylannulatomarin", *J. Asian Nat. Prod. Res.*, 12(1):88-93 (Taylor & Francis Group, Jan. 2010).

Wang, F. et al., "Atropisomeric bisoxazoline ligands with a bridge across the 5,5'-position of biphenyl for asymmetric catalysis", *Tetrahedron Letters*, 48(23):4083-4086 (Elsevier Ltd., 2007).

Wei, H. et al., "Novel atropisomeric bisphosphine ligands with a bridge across the 5,5'-position of the biphenyl for asymmetric catalysis", *Tetrahedron: Asymmetry*, 19(4):482-488 (Elsevier Ltd., 2008).

* cited by examiner

PROCESS-SCALE SYNTHESIS OF UROLITHINS

RELATED APPLICATION

This application claims benefit of priority from U.S. Provisional Patent Application No. 61/919,923, filed Dec. 23, 2013.

BACKGROUND

Pomegranate (*Punica granatum*) fruits have been used for centuries in folk medicine. They are consumed fresh and as juice, both of which are excellent sources of ellagitannins and ellagic acid. Ellagitannins (ETs) are polymeric polyphenols abundant in some fruits and nuts such as pomegranates, raspberries, strawberries, black raspberries, walnuts and almonds. Despite numerous reports of the biological properties and human health benefits of ETs, knowledge of their bioavailability, pharmacokinetics, disposition and metabolic fate in humans is limited. Commercially-produced pomegranate juice contains gallagyl-type ellagitannins, including punicalagin isomers (1500-1900 mg/L), undefined hydrolyzable tannins (400-500 mg/L), and ellagic acid and its glycosides (120-260 mg/L). Gil et al. *J. Agric. Food Chem.* 2000, 48, 4581-4589. Punicalagins, ellagitannins in which gallagic and ellagic acids are linked to a glucose molecule, are abundant in pomegranate peel. Punicalagin isomers and ellagic acid derivatives are not present in the aril juice, but during industrial juice processing they are extracted from the husk and membrane surrounding the arils and released in large quantities into the juice. The fruit arils of pomegranates contain other polyphenols, such as anthocyanins, responsible for the fruit's bright ruby-red color. Ellagitannins belong to a group of compounds known as hydrolyzable tannins, which release ellagic acid (EA) upon hydrolysis.

Unfortunately, ellagitannins are typically poorly absorbed by the human gut. However, a number of metabolites derived from ellagitannins are absorbed by the human gut, including certain metabolites ultimately formed in the gut by commensal microorganisms (i.e., intestinal microflora). Ellagitannins release ellagic acid under physiological conditions in vivo, and ellagic acid is then gradually metabolized by the gut microflora in the intestine to produce the urolithins. Once the metabolites are absorbed, they are further metabolized to produce urolithin glucuronides and/or sulfates. There is growing evidence that urolithins have potent antioxidant, anticancer, and anti-hyperproliferative activity. See US 2011/0065662; US 2012/0164243; and US 2014/0018415; all of which are incorporated by reference.

Although urolithins are derived from ETs present in certain foods (e.g., pomegranates), the consumption of these foods does not always lead to sufficient bioavailability of the therapeutic metabolites. Specifically, certain individuals, referred to herein as non-producers, fail to produce detectable amounts of the metabolites after consumption of ET-containing foods (e.g., pomegranate juice). Even among individuals who are producers, there is a great deal of variation (from very low to very high) in the amount of urolithin metabolites produced. Furthermore, any FDA-approved therapeutic use of urolithins would require a reliable and standard dosing regimen; that is, a known dose of a fully-characterized compound or compounds. It would thus be necessary to administer one or more selected urolithins directly to patients in need thereof.

In light of the therapeutic promise of urolithin compounds, a tremendous need exists for a safe, economical, reliable, and scalable synthesis approach to the urolithins. A reliable source of multi-kilo and commercial quantities of urolithin compounds will allow their further clinical development, with the ultimate goal of exploiting their full therapeutic potential.

SUMMARY OF THE INVENTION

One aspect of the present invention is a method for the preparation of urolithin compounds or intermediates useful in preparing such compounds or analogs thereof. Certain methods of the present invention include a copper-catalyzed coupling of two urolithin precursor fragments to form a coupling product (Method A). Certain methods of the present invention include demethylating one or more phenolic methoxy groups of a urolithin intermediate (Method B). In certain embodiments, Methods A and B are performed sequentially, but not necessarily in that order, to yield a urolithin or analog thereof. The present invention is improved over previous methods for producing the same or similar compounds (e.g., in terms of cost, yield, purity of the resulting product(s), catalyst loading, safety profile, reaction time, temperature, or amount/type of solvent used).

DETAILED DESCRIPTION

Figure 1:
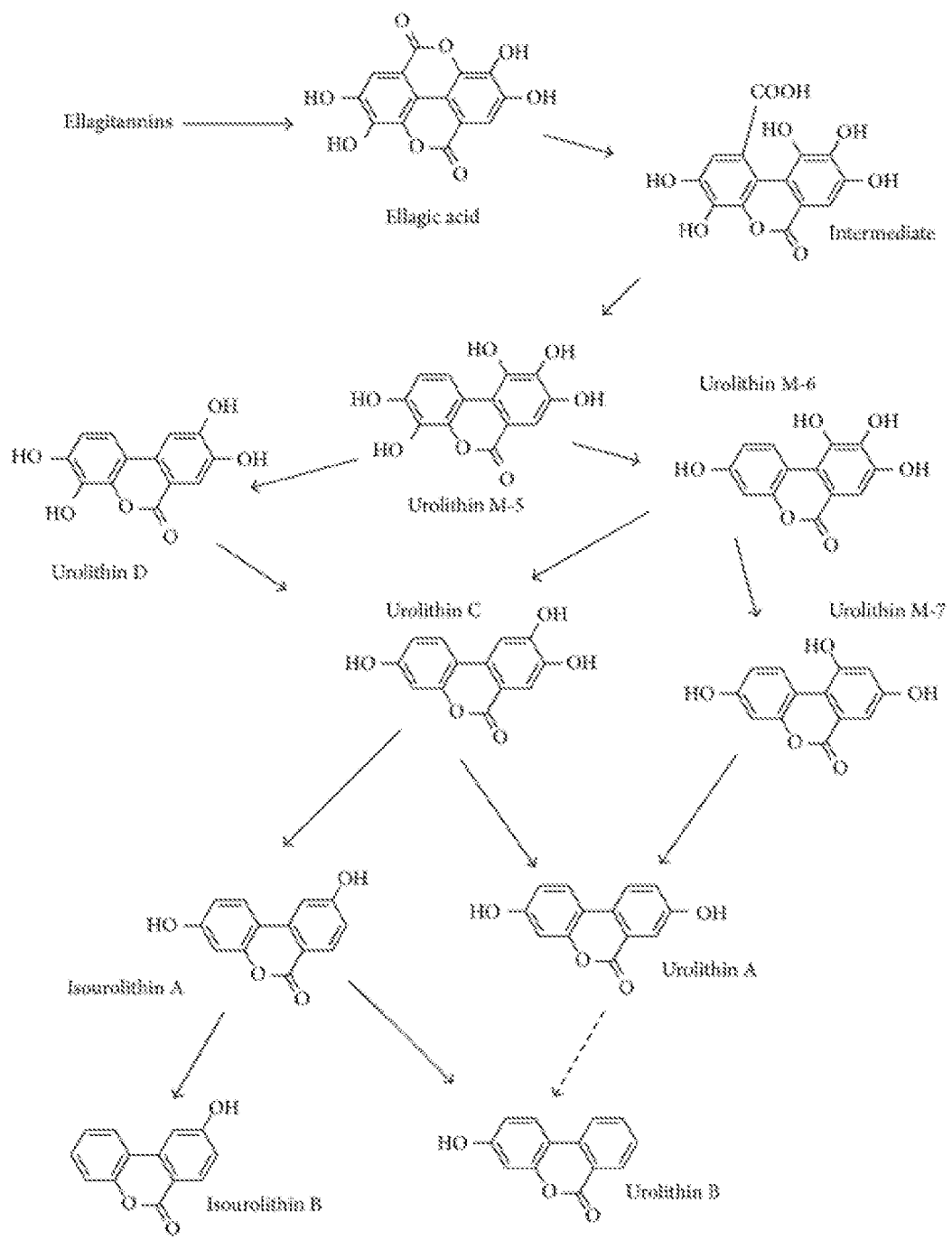
FIG. 1 shows the structures of exemplary urolithin compounds resulting from metabolism of ellagitannins.

As mentioned above, ellagitannins generally are not absorbed in the gut. Rather, they release ellagic acid (EA) in the gut, which is only poorly absorbed in the stomach and small intestine. EA is largely metabolized by unidentified bacteria in the intestinal lumen to produce urolithins. Urolithins are putative metabolites produced by human (or animal) gut microflora from ellagic acid, punicalagin (PA), punicalin (PB), tellimagrandin (TL), and other ellagitannins through a series of chemical modifications grouped into several pathways, giving rise to many known urolithins. In terms of chemical structure, urolithins are dibenzopyran-6-one derivatives with varying hydroxyl substitution patterns. The processing of ellagic acid begins with the loss of one of the two lactones present in ellagic acid (lactonase/decarboxylase activity), and is followed by optional removal of one or more hydroxyl groups (dehydroxylase activities) and optional further reactions including methylation and glycosylation.

More specifically, microbial metabolism of ellagic acid starts in the small intestine, and the first metabolites produced retain four phenolic hydroxyls (urolithin D, four hydroxyl groups; see FIG. 1); these are further metabolized along the intestinal tract to remove hydroxyl units leading to urolithin C (three hydroxyls), urolithin A (two hydroxyls) and B (one hydroxyl) in the distal parts of the colon. The absorbed metabolites are conjugated with glucuronic acid (one or two units), and/or methylated to form methyl ethers (e.g., when ortho-dihydroxyl groupings are present). Urolithin A and B conjugates are the main metabolites detected in plasma and urine, although some trihydroxy derivatives (hydroxyl-UA) or EA-dimethyl ether glucuronide have also been detected in smaller amounts. The tetrahydroxy-urolithins, trihydroxyurolithins, and EA derivatives generally are not detected in peripheral plasma, but they are absorbed in the small intestine and they are transported to the liver where they are further metabolized and excreted with bile to the small intestine, establishing an enterohepatic circulation that is responsible for the relatively long life of urolithins in plasma and urine.

Over the last twenty years many papers have appeared on the biosynthesis, isolation, and biological activity of tannins, especially ellagitannins. Access to pure ellagitannins by isolation from natural sources may be cumbersome and yield only relatively small quantities of pure natural products. See, for example, Okuda et al. (1982) Chem. Pharm. Bull. 30: 4230-4233; Okuda et al. (1982) Chem. Pharm. Bull. 30: 4234-4236. Methods are known for total synthesis of many ellagitannins. See, for example, Khanbabaee, K., Strategies for the synthesis of ellagitannins, In: Chemistry and Biology of Ellagitannins, Ed. S. Quideau, World Scientific Publishing, Singapore, 2009, pp. 152-202, including references cited therein.

The development of a process-scale synthesis of urolithins required substantial innovation. A useful process-scale synthesis must be efficient, cost-effective, and reproducible. Further, all starting materials and reagents must be reliably available in bulk, or able to be produced on site in a safe and economical fashion. The exacting regulatory standards for low impurity levels and overall safety of the process create additional challenges to development.

An Ullmann coupling is frequently used to couple the two phenyl rings present in all of the urolithin compounds. Unfortunately, the coupling routinely gives rise to product that is unacceptably contaminated with copper. The product also varies in color from batch to batch, from yellow to dark purple. Some residual copper may be removed by column chromatography; however, in process scale syntheses it is highly desirable to avoid column chromatography, due to its expense and large waste stream. Remarkably, improvements were made to a problematic Ullmann coupling. By drastically reducing the amount of copper catalyst, the isolated Ullmann coupling product consistently contained <1 ppm residual copper, and was off-white to light yellow in color. Moreover, the need for column chromatography was avoided.

A second improvement relates to a demethylation reaction. As discussed further in the Examples, the hydroxyl groups present in urolithins are often protected as methyl, ethyl, or alkyl ethers. Functionalizing the hydroxyl groups as ethers also allows access to a variety of more lipophilic and potentially more-bioavailable urolithin analogs. To allow access to the natural urolithins, demethylation/dealkylation of the ethers must be performed. This transformation has frequently been accomplished on similar substrates with $BBr_3$ (boron tribromide), a chemical reagent associated with various hazards and drawbacks. Remarkably, it was discovered that the powerful Lewis acid $AlCl_3$ (aluminum trichloride) can bring about the desired transformation in greater than 40%, greater than 50%, greater than 60%, greater than 70%, greater than 80%, greater than 85%, or even greater than 88% yield. Subsequent hydrolysis of the excess $AlCl_3$, filtration, and a recrystallization provided the pure demethylated product containing <17 ppm aluminum.

Definitions

A number of abbreviations and defined terms are used in this application. Explanations and their definitions appear below.

As used herein, compounds which are "commercially available" may be obtained, e.g., from standard commercial sources.

As used herein, "suitable conditions" for carrying out a synthetic step are explicitly provided herein, or may be discerned by reference to publications directed to methods used in synthetic organic chemistry, or are generally known to one of ordinary skill in the art. The reference books and detailed description set forth below that describe the synthesis of intermediates useful in the preparation of compounds of the present invention will also provide suitable conditions for carrying out a synthetic step according to the present invention.

"Stable compound" and "stable structure" are meant to indicate a compound that is sufficiently robust to survive isolation to a useful degree of purity from a reaction mixture, and/or formulation into an efficacious therapeutic agent.

"Optional" or "optionally" means that the subsequently described event or circumstances may or may not occur, and that the description includes instances where said event or circumstance occurs and instances in which it does not. For example, "optionally substituted aryl" means that the aryl radical may or may not be substituted, and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals, and as used herein also encompasses any agent suitable for use as a food additive.

"Pharmaceutically acceptable salt" includes both acid and base addition salts. "Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, and choline.

The term "base" as used herein may include any inorganic or organic base selected from those mentioned above in addition to non-pharmaceutically acceptable bases that are efficacious in organic chemistry. Particularly preferred organic bases are isopropylamine, diethylamine, ethanolamine, trimethylamine, diisopropylethylamine (DIPEA), dicyclohexylamine, 1,4-diazabicyclo[2.2.2]octane (DABCO), 1,8-Bis (dimethylamino)naphthalene (Proton Sponge), and 1,8-Diazabicyclo[5.4.0]undec-7-ene (DBU).

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

The term "alkyl" as used herein is intended to include linear, branched, or cyclic hydrocarbon structures and combinations thereof. Lower alkyl (or haloalkyl) refers to alkyl (haloalkyl) groups of from 1 to 6 carbon atoms. Examples of lower alkyl groups include methyl, ethyl, propyl, isopropyl, butyl, s- and t-butyl and the like. Preferred alkyl groups are those of $C_{20}$ or below. More preferred alkyl groups are those of $C_{12}$ or below. Cycloalkyl is a subset of alkyl and includes cyclic hydrocarbon groups of from 3 to 12 carbon atoms. Examples of cycloalkyl groups include c-propyl, c-butyl, c-pentyl, norbornyl, adamantyl and the like. The terms "alkenyl" and "alkynyl" have identical chain lengths as mentioned above for "alkyl", but have one or more double or triple bonds in the carbon chain or at the two terminal positions of the carbon chain, respectively. "Alkylene" refers to the same residues as alkyl, but having two points of attachment. Examples of alkylene include ethylene (—$CH_2CH_2$—), propylene (—$CH_2CH_2CH_2$—), dimethylpropylene (—$CH_2C(CH_3)_2CH_2$—) and cyclohexylpropylene (—$CH_2CH_2CH(C_6H_{13})$—). When an alkyl residue having a specific number of carbons is named, all geometric isomers having that number of carbons are intended to be encompassed; thus, for example, "butyl" is meant to include cyclobutyl, n-butyl, sec-butyl, isobutyl and t-butyl; "propyl" includes cyclopropyl, n-propyl and isopropyl.

"Alkoxy" or "alkoxyl" refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower alkoxy refers to groups containing one to four carbons.

"Acyl" refers to groups of from 1 to 8 carbon atoms of a straight, branched or cyclic configuration, or a combination of any such configurations, attached to the parent structure through a carbonyl functionality. Such acyl groups can be saturated or unsaturated, and aromatic or non-aromatic. One or more carbons in the acyl residue can be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower acyl refers to groups containing one to four carbons.

"Aryl" means a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene, naphthalene, indane, tetralin, and fluorine, and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

"Aralkyl" refers to a residue in which an aryl moiety is attached to an alkyl residue. Examples are benzyl, phenethyl, phenylvinyl, phenylallyl and the like.

"Oxaalkyl" and "oxaaralkyl" refer to alkyl and aralkyl residues in which one or more methylenes have been replaced by oxygen. Examples of oxaalkyl and oxaalkylaryl residues are ethoxyethoxyethyl (3,6-dioxaoctyl), benzyloxymethyl and phenoxymethyl; in general, glycol ethers, such as polyethyleneglycol, are intended to be encompassed by this group.

"Heteroaralkyl" refers to a residue in which a heteroaryl moiety is attached to the parent structure via an alkyl residue. Examples include furanylmethyl, pyridinylmethyl, pyrimidinylethyl and the like.

"Heterocyclyl" means a cycloalkyl or aryl residue in which one to four of the carbons is replaced by a heteroatom, such as oxygen, nitrogen or sulfur. Examples of heterocycles that fall within the scope of the invention include imidazoline, pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. "N-heterocyclyl" refers to a nitrogen-containing heterocycle as a substituent residue. The term heterocyclyl encompasses heteroaryl, which is a subset of heterocyclyl. Examples of N-heterocyclyl residues include 4-morpholinyl, 4-thiomorpholinyl, 1-piperidinyl, 1-pyrrolidinyl, 3-thiazolidinyl, piperazinyl and 4-(3,4-dihydrobenzoxazinyl). Examples of substituted heterocyclyl include 4-methyl-1-piperazinyl and 4-benzyl-1-piperidinyl.

Substituted alkyl, aryl and heteroaryl refer to alkyl, aryl or heteroaryl wherein one or more hydrogen atom(s) is replaced with alkyl, halogen, hydroxy, alkoxy, alkylenedioxy (e.g., methylenedioxy) fluoroalkyl, carboxy (—COOH), carboalkoxy (i.e., acyloxy RCOO—), carboxyalkyl (—COOR), carboxamido, sulfonamidoalkyl, sulfonamidoaryl, aminocarbonyl, benzyloxycarbonylamino (CBZ-amino), cyano, carbonyl, nitro, dialkylamino, alkylamino, amino, alkylthio, alkylsulfinyl, alkylsulfonyl, alkylsulfonamido, arylthio, arylsulfinyl, arylsulfonyl, amidino, phenyl, benzyl, heteroaryl, heterocyclyl, substituted heterocyclyl, phenoxy, benzyloxy, or heteroaryloxy. For the purposes of the present invention, substituted alkyl also includes oxaalkyl residues, i.e., alkyl residues in which one or more carbons has been replaced by oxygen. Preferred substitutions include alkyl, alkenyl, alkynyl, halogen, hydroxy, alkoxy, fluoroalkyl, cyano, carbonyl, nitro, dialkylamino, alkylamino, amino, alkylthio, aralkyl, heteroaryl, and heterocyclyl.

"Halogen" refers to fluorine, chlorine, bromine or iodine. Fluorine, chlorine and bromine are preferred. Dihaloaryl, dihaloalkyl, trihaloaryl etc. refer to aryl and alkyl substituted with a plurality of halogens, but not necessarily a plurality of the same halogen; thus 4-chloro-3-fluorophenyl is within the scope of dihaloaryl.

As used herein, the term "monosaccharide" refers to a simple sugar of the formula $(CH_2O)_n$. The monosaccharides can be straight-chain or ring systems, and can include a saccharose unit of the formula —CH(OH)—C(=O)—. Examples of monosaccharides include erythrose, threose, ribose, arabinose, xylose, lyxose, allose, altrose, glucose, mannose, gulose, idose, galactose, talose, erythulose, ribulose, xyulose, psicose, fructose, sorbose, tagatose, erythropentulose, threopentulose, glycerotetrulose, glucopyranose, fructofuranose. In certain embodiments, monosaccharide refers to glucopyranose.

As used herein, the term "oligosaccharide" refers to saccharide consisting of at least two, up to 10 glycosidically linked monosaccharide units, preferably of 2 to 8 monosaccharide units, more preferably of 2 to 7 monosaccharide units, and even more preferably of 2 to 6 monosaccharide units or of 2 to 5 monosaccharide units.

The terms "solvent", "inert organic solvent" or "inert solvent" mean a solvent inert under the conditions of the reaction being described in conjunction therewith. Solvents employed in synthesis of the compounds of the invention include, for example, methanol, acetone, water, acetonitrile, 1,4-dioxane, dimethylformamide, benzene, toluene, tetrahydrofuran, chloroform, methylene chloride (or dichloromethane), diethyl ether, tert-butyl methyl ether (TBME), pyridine and the like, as well as mixtures thereof. Unless specified to the contrary, the solvents used in the reactions of the present invention are inert organic solvents.

As used herein, the term "hydroxyl" means —OH.
As used herein, the term "nitro" means —$NO_2$.
As used herein, the term "thiol" means —SH.
As used herein, the term "sulfonyl" means —$SO_2$—.
As used herein, the term "disulfide" refers to any chemical compound that comprises a covalently linked pair of sulfur atoms (disulfide bond), e.g., diphenyl disulfide ($C_6H_5$—S—S—$C_6H_5$).

The terms "amine" and "amino" are art-recognized and refer to both unsubstituted and substituted amines, e.g., a moiety that can be represented by the general formula:

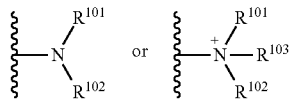

wherein $R^{101}$, $R^{102}$ and $R^{103}$ each independently represent hydrogen, alkyl, alkenyl, alkynyl, aryl, heteroaryl, —$(CH_2)_m R^{200}$, wherein m is an integer 1-10 and $R^{200}$ represents a group permitted by the rules of valence, such as hydrogen, alkyl, alkenyl, alkynyl, aryl, and heteroaryl.

The term "amino" also includes "acylamino," which is art-recognized and refers to a moiety that can be represented by the general formula:

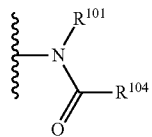

wherein $R^{101}$ is as defined above, and $R^{104}$ represents hydrogen, alkyl, alkenyl, alkynyl, aryl, heteroaryl or —$(CH_2)_m R^{200}$, wherein m and $R^{200}$ are defined above.

The term "amido" is art-recognized as an amino-substituted carbonyl and includes a moiety that can be represented by the general formula:

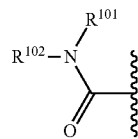

wherein $R^{101}$ and $R^{102}$ are as defined above. Preferred embodiments of the amide will not include those which are unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R^{200}$, wherein m and $R^{200}$ are defined above. Representative alkylthio groups include methylthio and ethylthio.

The term "carbonyl" is art-recognized and includes such moieties as can be represented by the general formula:

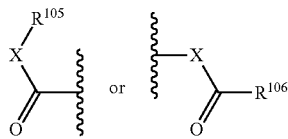

wherein X is a bond or represents an oxygen or a sulfur, and $R^{105}$ represents a hydrogen, alkyl, alkenyl, alkynyl, aryl, heteroaryl or —$(CH_2)_m R^{200}$, wherein m and $R^{200}$ are defined above, or a pharmaceutically acceptable salt, and $R^{106}$ represents hydrogen, alkyl, alkenyl, alkynyl, aryl, heteroaryl or —$(CH_2)_m R^{200}$, wherein m and $R^{200}$ are defined above. Where X is oxygen and $R^{105}$ or $R^{106}$ is not hydrogen, the formula represents an "ester". Where X is oxygen and $R^{105}$ is as defined above, the moiety is referred to herein as a carboxyl group, and particularly when $R^{105}$ is hydrogen, the formula represents a "carboxylic acid". Where X is oxygen and $R^{106}$ is hydrogen, the formula represents a "formate". In general, where the oxygen atom of the above formula is replaced by sulfur, the formula represents a "thiocarbonyl" group. Where X is a sulfur and $R^{105}$ or $R^{106}$ is not hydrogen, the formula represents a "thioester." Where X is sulfur and $R^{105}$ is hydrogen, the formula represents a "thiolcarboxylic acid." Where X is a sulfur and $R^{106}$ is hydrogen, the formula represents a "thiolformate." On the other hand, where X is a bond and $R^{105}$ is not hydrogen, the above formula represents a "ketone" group. Where X is a bond, and $R^{106}$ is hydrogen, the above formula represents an "aldehyde" group.

The terms "alkoxyl" or "alkoxy" as used herein refer to an alkyl group, as defined above, having an oxygen radical attached thereto. Representative alkoxyl groups include methoxy, ethoxy, propyloxy, t-butoxy and the like.

An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, and —$(CH_2)_m$—$R^{200}$, where m and $R^{200}$ are as defined above.

The term "heteroatom" as used herein means an atom of any element other than carbon or hydrogen. Preferred heteroatoms are nitrogen, oxygen, sulfur, phosphorus and selenium. In one embodiment, a heteroatom is selected from nitrogen, oxygen, and sulfur. In one embodiment, a heteroatom is selected from nitrogen and oxygen. In one embodiment, a heteroatom is nitrogen. In one embodiment, a heteroatom is oxygen.

The isolation and purification procedures described herein can be effected, if desired, by any suitable separation or purification procedure such as, for example, filtration, extraction, crystallization, column chromatography, thin-layer chromatography or preparative chromatography, or a combination of these procedures. Specific illustrations of suitable separation and isolation procedures can be had by reference to the examples below. However, other equivalent separation or isolation procedures can, of course, also be used.

Methods of the Invention

One aspect of the present invention relates to a method of preparing a compound of formula I, comprising the step of combining in an aqueous alkaline solvent mixture a copper-containing catalyst, a compound of formula II, and a compound of formula III, thereby forming the compound of formula I;

wherein
the compound of formula I is represented by:

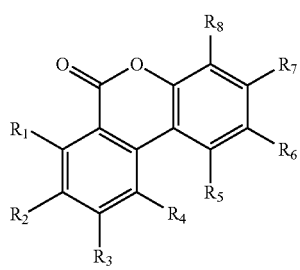

(I)

$R_1$, $R_2$, $R_3$, $R_4$, $R_5$, $R_6$, $R_7$, and $R_8$ are, independently for each occurrence, selected from the group consisting of H, alkyl, haloalkyl, heteroalkyl, alkenyl, alkynyl, halogen, and OR; wherein, if two OR are present at adjacent positions, then the two R groups taken together may represent a methylene (—$CH_2$—) group;

R is selected from the group consisting of H, lower alkyl, lower haloalkyl, acyl, aracyl, sulfate, monosaccharide, and oligosaccharide;

the compound of formula II is represented by:

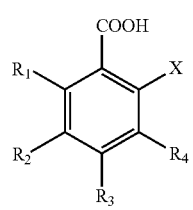

(II)

or an alkyl or aryl ester thereof; wherein X is selected from the group consisting of Cl, Br, and I; and the compound of formula III is represented by:

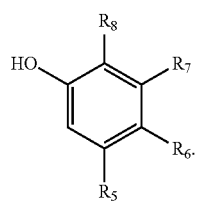

(III)

In certain embodiments, the copper-containing catalyst is selected from the group consisting of copper powder, copper-bronze couple, $CuSO_4$ hydrate, anhydrous $CuSO_4$, $Cu(acac)_2$, CuCl, $CuCl_2$, CuBr, $CuBr_2$, CuI, $Cu_2O$, CuO, CuOTf, CuCN, and mixtures thereof.

In certain embodiments, the copper-containing catalyst is selected from the group consisting of copper powder, copper-bronze couple, $CuSO_4$ hydrate, anhydrous $CuSO_4$, $Cu(acac)_2$, CuCl, $CuCl_2$, CuBr, $CuBr_2$, CuI, and mixtures thereof.

In certain embodiments, the copper-containing catalyst is selected from the group consisting of copper powder, $CuSO_4$ hydrate, anhydrous $CuSO_4$, $CuCl_2$, $CuBr_2$, CuI, and mixtures thereof.

In certain embodiments, the copper-containing catalyst is $CuSO_4$ hydrate or anhydrous $CuSO_4$.

In certain embodiments, the amount of copper-containing catalyst is at least a trace amount but less than 0.05 equivalents relative to either formula II or formula III.

In certain embodiments, the amount of copper-containing catalyst is at least a trace amount but less than 0.02 equivalents relative to either formula II or formula III.

In certain embodiments, the amount of copper-containing catalyst is at least a trace amount but less than 0.01 equivalents relative to either formula II or formula III.

In certain embodiments, the amount of copper-containing catalyst is at least a trace amount but less than 0.005 equivalents relative to either formula II or formula III.

In certain embodiments, the amount of copper-containing catalyst is at least a trace amount but less than 0.001 equivalents relative to either formula II or formula III.

In certain embodiments, the amount of copper-containing catalyst is at least a trace amount but less than 0.0005 ($5\times 10^{-4}$) equivalents relative to either formula II or formula III.

In certain embodiments, the amount of copper-containing catalyst is at least a trace amount but less than 0.0001 ($1\times 10^{-4}$) equivalents relative to either formula II or formula III.

In certain embodiments, the aqueous alkaline solvent comprises LiOH, NaOH, KOH, CsOH, $Na_2CO_3$, $CaCO_3$, or $Cs_2CO_3$.

In certain embodiments, the aqueous alkaline solvent comprises NaOH or KOH.

In certain embodiments, the method is conducted at a temperature from about 20° C. to about 180° C.

In certain embodiments, the method is conducted at a temperature from about 40° C. to about 130° C.

In certain embodiments, the method is conducted at a temperature from about 50° C. to about 110° C.

In certain embodiments, the method is conducted at a temperature from about 70° C. to about 90° C.

In certain embodiments, at least 95% of formula II or formula III is consumed in about 0.5 to about 10 hours.

In certain embodiments, at least 95% of formula II or formula III is consumed in about 1 to about 8 hours.

In certain embodiments, at least 95% of formula II or formula III is consumed in about 2 to about 6 hours.

In certain embodiments, the yield of formula I is at least about 40% relative to the limiting reagent between formula II and formula III.

In certain embodiments, the yield of formula I is at least about 50% relative to the limiting reagent between formula II and formula III.

In certain embodiments, the yield of formula I is at least about 60% relative to the limiting reagent between formula II and formula III.

In certain embodiments, the yield of formula I is at least about 70% relative to the limiting reagent between formula II and formula III.

In certain embodiments, the yield of formula I is at least about 80% relative to the limiting reagent between formula II and formula III.

In certain embodiments, the yield of formula I is at least about 85% relative to the limiting reagent between formula II and formula III.

In certain embodiments, formula I is formed in a purity of at least about 90%.

In certain embodiments, formula I is formed in a purity of at least about 95%.

In certain embodiments, formula I is formed in a purity of at least about 98%.

In certain embodiments, formula I contains less than about 50 ppm copper.

In certain embodiments, formula I contains less than about 25 ppm copper.

In certain embodiments, formula I contains less than about 10 ppm copper.

In certain embodiments, formula I contains less than about 5 ppm copper.

In certain embodiments, formula I contains less than about 1 ppm copper.

In certain embodiments, X is selected from the group consisting of Cl, Br, and I.

In certain embodiments, X is Br.

In certain embodiments, the method is represented by:

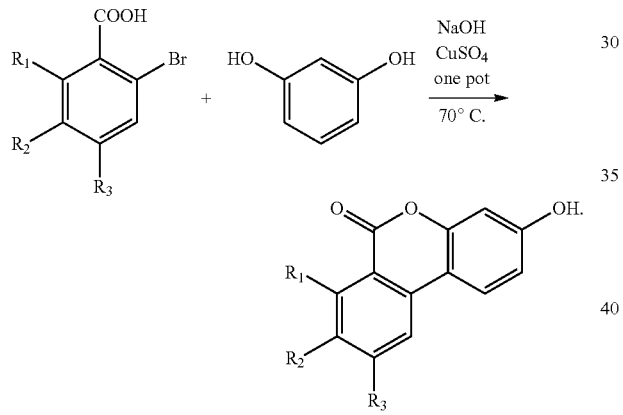

In certain embodiments, $R_1$, $R_2$, $R_3$, $R_4$, $R_5$, $R_6$, $R_7$, and $R_8$ are, independently for each occurrence, selected from the group consisting of H, alkyl, haloalkyl, and OR.

In certain embodiments, $R_1$, $R_2$, $R_3$, $R_4$, $R_5$, $R_6$, $R_7$, and $R_8$ are, independently for each occurrence, H or OR; and R is H or lower alkyl.

In certain embodiments, $R_2$ is H or OMe.

In certain embodiments, $R_1$, $R_4$, $R_5$, $R_6$, and $R_8$ are each H.

In certain embodiments, $R_2$ is OMe; and $R_3$, $R_7$, and $R_8$ are each OH or OMe.

In certain embodiments, $R_1$, $R_3$, $R_4$, $R_5$, $R_6$, and $R_8$ are each H; $R_2$ is OMe; and $R_7$ is OH;

$R_1$, $R_3$, $R_4$, $R_5$, $R_6$, $R_7$, and $R_8$ are each H; and $R_2$ is OMe;

$R_1$, $R_4$, $R_5$, $R_6$, and $R_8$ are each H; $R_2$ is OMe; and $R_3$ and $R_7$ are each OH; or $R_1$, $R_4$, $R_5$, and $R_6$ are each H; $R_2$ is OMe; and $R_3$, $R_7$, and $R_8$ are each OH.

In certain embodiments, $R_1$, $R_3$, $R_4$, $R_5$, $R_6$, and $R_8$ are H; $R_2$ is OMe; and $R_7$ is OH.

In certain embodiments, $R_1$, $R_2$, $R_3$, $R_4$, $R_5$, $R_6$, and $R_8$ are H; and $R_7$ is OH.

One aspect of the present invention relates to a method of preparing a compound of formula IV, comprising the step of combining an inert organic solvent, a compound of formula V, and a Lewis acid selected from the group consisting of $AlCl_3$, $AlBr_3$, $BeCl_2$, $FeCl_3$, and $SiCl_4$; thereby forming the compound of formula IV;

wherein the compound of formula IV is represented by:

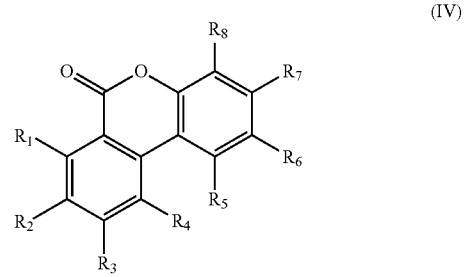

wherein:

$R_1$, $R_2$, $R_3$, $R_4$, $R_5$, $R_6$, $R_7$, and $R_8$ are, independently for each occurrence, selected from the group consisting of H, alkyl, haloalkyl, heteroalkyl, alkenyl, alkynyl, halogen, and OR; and R is selected from the group consisting of H, acyl, aracyl, sulfate, monosaccharide, and oligosaccharide; and the compound of formula V is represented by:

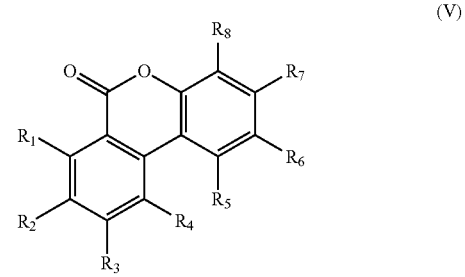

wherein:

$R_1$, $R_2$, $R_3$, $R_4$, $R_5$, $R_6$, $R_7$, and $R_8$ are, independently for each occurrence, selected from the group consisting of H, alkyl, haloalkyl, heteroalkyl, alkenyl, alkynyl, halogen, and OR; wherein, if two OR are present at adjacent positions, then the two R groups taken together may be a methylene (—$CH_2$—) group; and R is selected from the group consisting of H, lower alkyl, lower haloalkyl, acyl, aracyl, sulfate, monosaccharide, and oligosaccharide;

with the provisos that (i) at least one of $R_1$, $R_2$, $R_3$, $R_4$, $R_5$, $R_6$, $R_7$, and $R_8$ in formula IV is OH; and (ii) at least one of $R_1$, $R_2$, $R_3$, $R_4$, $R_5$, $R_6$, $R_7$, and $R_8$ in formula V is O-alkyl.

In certain embodiments, the Lewis acid is $AlCl_3$ or $AlBr_3$.

In certain embodiments, the Lewis acid is $AlCl_3$.

In certain embodiments, the method may further comprise an additive selected from the groups consisting of a $C_2$-$C_{24}$ thiol, LiCl, NaI, tetrabutylammonium iodide ($Bu_4NI$), NaOMe, and trimethylamine hydrochloride.

In certain embodiments, the additive is ethanethiol.

In certain embodiments, the mixture is heated to a temperature of about 50 to about 120° C.

In certain embodiments, the mixture is heated to a temperature of about 60 to about 110° C.

In certain embodiments, the mixture is heated to a temperature of about 70 to about 100° C.

In certain embodiments, the starting material is contacted with the Lewis acid for about 30 minutes to about 5 hours.

In certain embodiments, the starting material is contacted with the Lewis acid for about 1 hour to about 2 hours.

In certain embodiments, the compound of formula IV is formed in at least 40% yield relative to the compound of formula V.

In certain embodiments, the compound of formula IV is formed in at least 50% yield relative to the compound of formula V.

In certain embodiments, the compound of formula IV is formed in at least 60% yield relative to the compound of formula V.

In certain embodiments, the compound of formula IV is formed in at least 70% yield relative to the compound of formula V.

In certain embodiments, the compound of formula IV is formed in at least 80% yield relative to the compound of formula V.

In certain embodiments, the compound of formula IV is formed in at least 85% yield relative to the compound of formula V.

In certain embodiments, the inert organic solvent is selected from the group consisting of dichloromethane, dichloroethane, chloroform, carbon tetrachloride, chlorobenzene, diethyl ether, 1,4-dioxane, tert-butyl methyl ether (TBME), tetrahydrofuran (THF), N,N-dimethylformamide (DMF), N-methylpyrrolidone (NMP), diglyme, nitromethane, 1,2-dimethoxyethane (DME), pyridine, ethyl acetate, acetone, acetonitrile, benzene, o-xylene, m-xylene, p-xylene, xylenes, hexanes, cyclohexane, heptane, octane, nonane, and decane.

In certain embodiments, the inert organic solvent is selected from the group consisting of chlorobenzene, 1,4-dioxane, tert-butyl methyl ether (TBME), tetrahydrofuran (THF), 1,2-dimethoxyethane (DME), pyridine, benzene, toluene, o-xylene, m-xylene, p-xylene, and xylenes.

In certain embodiments, the inert organic solvent is selected from the group consisting of chlorobenzene, benzene, toluene, o-xylene, m-xylene, p-xylene, and xylenes.

In certain embodiments, the inert organic solvent is toluene.

In certain embodiments, the method described above may further comprise the step of recrystallizing the compound of formula IV from an organic acid selected from the group consisting of formic acid, acetic acid, chloroacetic acid, dichloroacetic acid, trichloroacetic acid, and trifluoroacetic acid.

In certain embodiments, the organic acid is acetic acid.

In certain embodiments, $R_1$, $R_2$, $R_3$, $R_4$, $R_5$, $R_6$, $R_7$, and $R_8$ are, independently for each occurrence, selected from the group consisting of H, alkyl, haloalkyl, and OR.

In certain embodiments, $R_1$, $R_2$, $R_3$, $R_4$, $R_5$, $R_6$, $R_7$, and $R_8$ are, independently for each occurrence, H or OR; and R is H or lower alkyl.

In certain embodiments, $R_2$ is H or OMe.

In certain embodiments, $R_1$, $R_4$, $R_5$, $R_6$, and $R_8$ are each H.

In certain embodiments, $R_2$ is OMe; and $R_3$, $R_7$, and $R_8$ are each OH or OMe.

In certain embodiments, in the compound of formula IV:
$R_1$, $R_3$, $R_4$, $R_5$, $R_6$, and $R_8$ are each H; $R_2$ and $R_7$ are both OH;

$R_1$, $R_3$, $R_4$, $R_5$, $R_6$, $R_7$, and $R_8$ are each H; and $R_2$ is OH;

$R_1$, $R_4$, $R_5$, $R_6$, and $R_8$ are each H; and $R_2$, $R_3$, and $R_7$ are each OH; or $R_1$, $R_4$, $R_5$, and $R_6$ are each H; $R_2$, $R_3$, $R_7$, and $R_8$ are each OH.

In certain embodiments, in the compound of formula IV: $R_1$, $R_3$, $R_4$, $R_5$, $R_6$, and $R_8$ are H, and $R_2$ and $R_7$ are both OH.

In certain embodiments, in the compound of formula IV: $R_1$, $R_2$, $R_3$, $R_4$, $R_5$, $R_6$, and $R_8$ are H; and $R_7$ is OH.

One aspect of the present invention relates to a method of preparing a compound of formula IV, comprising performing first the method described above of forming a compound of formula I; and then the method described above wherein formula V is reacted to form the compound of formula IV.

Compositions of the Invention

An aspect of the invention is a composition, comprising copper and a compound of formula I:

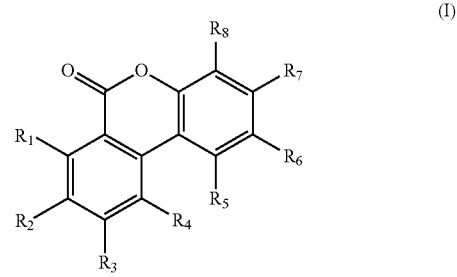

wherein
$R_1$, $R_2$, $R_3$, $R_4$, $R_5$, $R_6$, $R_7$, and $R_8$ are, independently for each occurrence, selected from the group consisting of H, alkyl, haloalkyl, heteroalkyl, alkenyl, alkynyl, halogen, and OR; wherein, if two OR are present at adjacent positions, then the two R groups taken together may represent a methylene (—CH$_2$—) group; and R is selected from the group consisting of H, lower alkyl, lower haloalkyl, acyl, aracyl, sulfate, monosaccharide, and oligosaccharide;

wherein the composition comprises <50 ppm copper.

In certain embodiments, $R_1$, $R_2$, $R_3$, $R_4$, $R_5$, $R_6$, $R_7$, and $R_8$ are, independently for each occurrence, selected from the group consisting of H, alkyl, haloalkyl, and OR.

In certain embodiments, $R_1$, $R_2$, $R_3$, $R_4$, $R_5$, $R_6$, $R_7$, and $R_8$ are, independently for each occurrence, H or OR; and R is H or lower alkyl.

In certain embodiments, $R_2$ is H or OMe.

In certain embodiments, $R_1$, $R_4$, $R_5$, $R_6$, and $R_8$ are each H.

In certain embodiments, $R_2$ is OMe; and $R_3$, $R_7$, and $R_8$ are each OH or OMe.

In certain embodiments,
$R_1$, $R_3$, $R_4$, $R_5$, $R_6$, and $R_8$ are each H; $R_2$ is OMe; and $R_7$ is OH;

$R_1$, $R_3$, $R_4$, $R_5$, $R_6$, $R_7$, and $R_8$ are each H; and $R_2$ is OMe;

$R_1$, $R_4$, $R_5$, $R_6$, and $R_8$ are each H; $R_2$ is OMe; and $R_3$ and $R_7$ are each OH; or $R_1$, $R_4$, $R_5$, and $R_6$ are each H; $R_2$ is OMe; and $R_3$, $R_7$, and $R_8$ are each OH.

In certain embodiments, $R_1$, $R_3$, $R_4$, $R_5$, $R_6$, and $R_8$ are each H; $R_2$ is OMe; and $R_7$ is OH.

In certain embodiments, $R_1$, $R_2$, $R_3$, $R_4$, $R_5$, $R_6$, and $R_8$ are H; and $R_7$ is OH.

In certain embodiments, the composition comprises <25 ppm copper.

In certain embodiments, the composition comprises <10 ppm copper.

In certain embodiments, the composition comprises <5 ppm copper.

In certain embodiments, the composition comprises <1 ppm copper.

EXEMPLIFICATION

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. The invention now being generally described, it will be more readily understood by reference to the following, which is included merely for purposes of illustration of certain aspects and embodiments of the present invention, and is not intended to limit the invention.

Example 1

Ullmann-Type Coupling of a Halogenated Benzoic Acid with a (Di)Hydroxybenzene

Described herein is the first step in a short and practical synthesis of urolithins beginning with the commercially available reagents 2-bromo-5-methoxy benzoic acid and resorcinol. This step is an Ullmann reaction and is applicable to a variety of alternate precursors leading to other urolithin intermediates.

The Ullmann reaction, or Ullmann coupling, is a reductive coupling of aryl halides discovered over 100 years ago. Classically, this reaction requires a stoichiometric copper catalyst, extended reaction times, and extremely harsh conditions. An active copper powder that is required for this reaction can be prepared by the reduction of copper sulfate by zinc metal in hot water causing the precipitation of elementary copper. The reaction often requires high-boiling polar solvents such as N-methylpyrrolidone, nitrobenzene or dimethylformamide and high temperatures (often in excess of 210° C.) with stoichiometric amounts of copper. The aryl halide is activated by electron-withdrawing groups or carries a carboxylic acid group in the aromatic ortho position. Furthermore, the Ullmann reaction is often unreliable, giving unpredictable yields, purity of product, and conversion of the starting materials. Extensive research efforts have yielded some improvements (including the use of copper-coordinating ligands) and alternate, sometimes milder, conditions, but the reaction's unpredictable nature remains (see, for example, J. Hassan et al. "Aryl-Aryl Bond Formation One Century after the Discovery of the Ullmann Reaction" *Chemical Reviews* 102 (5): 1359-1470. (2002)). Thus, extensive efforts must be undertaken to discover and optimize conditions for the successful use of the Ullmann reaction on a case-by-case basis.

As a late transition element, copper occurs in a range of oxidation states (Cu(0), Cu(I), Cu(II), Cu(III) and Cu(IV)), and the ions readily form complexes yielding a variety of coordination compounds. Oxidation states I and II are known for many compounds and are the most common, while compounds with copper in oxidation state III are fewer in number. Compounds containing Cu(0) species have been observed under particular conditions and oxidation state IV exists only in a specific environment, in fluorides and oxides. Generally speaking, copper catalysts in the 0, I and II oxidation states can work well in Ullmann couplings.

A related type of coupling reaction is the Hurtley reaction, in which a haloarene is coupled with a carbon nucleophile (usually β-diketone) under copper catalysis in the presence of an appropriate base. In the reaction as originally reported the arene was 2-bromobenzoic acid, the carbon nucleophile was a malonic ester or other dicarbonyl compound and the base was sodium ethoxide (NaOEt). In this case the carbon nucleophile is aromatic, and the C—H bond to be deprotonated is sp³ hybridized and is adjacent (ortho) to a phenolic OH group.

The successful development of improved catalytic versions of this venerable reaction has led to its renaissance, with the various improved embodiments collectively known as the 'modified Ullmann reaction'. Many drawbacks of the classical reaction (e.g., the high reaction temperatures, long reaction times, high metal loadings, and narrow scope) have been overcome and a wide range of new procedures became available for applications in many areas. The key of the 'modified Ullmann' procedure lies in the addition of ligands to the copper catalyst in order to improve the solubility of the copper precursors, leading to the use of milder reaction conditions, i.e., lower reaction temperature and time, lower catalyst loadings, and a widened scope of reactivity. In general the copper (pre-) catalyst is prepared by the in situ mixing of a copper salt and a suitable, often bidentate, chelator such as diamines, amino acids, 1,10-phenanthrolines, diols and other nitrogen- and oxygen-containing ligands. These developments have been so successful that the modified Ullmann reaction has already found its way into large-scale production. It is clear that this technology is much cheaper than the highly successful palladium-catalyzed variants. There is one major difference, however; whereas the palladium-catalyzed Hartwig-Buchwald arylation is mechanistically well-understood there appears to be no consensus yet on the mechanism of the modified Ullmann reaction.

A generalized scheme for the present improved Ullmann coupling is shown below. At first, approximately 0.15 g of CuSO₄ per gram of carboxylic acid starting material was used. Ullman couplings reported in the chemical literature on similar substrates reported as little as half that amount of copper, but yields for the desired transformation average around 60%, suggesting that using less copper catalyst would erode the yield due to lower conversion of the starting materials. Moreover, when 0.15 g copper per gram of starting material was used the coupling product was unfailingly isolated with significant (greater than about 100 ppm) copper contamination. Efforts to reduce or remove copper contamination were unsuccessful. Even if a method could be found of purifying the product to have sufficiently low copper levels for use of the product as an active pharmaceutical ingredient (API), it would greatly increase the cost and inefficiency of the resulting manufacturing process. In fact, no reported method can supply the desired Ullmann coupling products without a high degree of copper contamination. Of course, to obtain regulatory approval for use in humans all pharmaceutical compounds must be manufactured with impurity levels (particularly heavy metals) at low, reproducible levels.

Scheme 1 - General Reaction Scheme

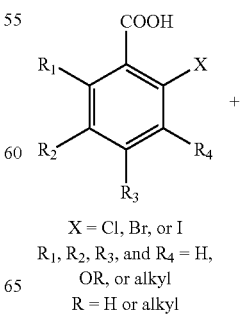

X = Cl, Br, or I
$R_1$, $R_2$, $R_3$, and $R_4$ = H, OR, or alkyl
R = H or alkyl -continued

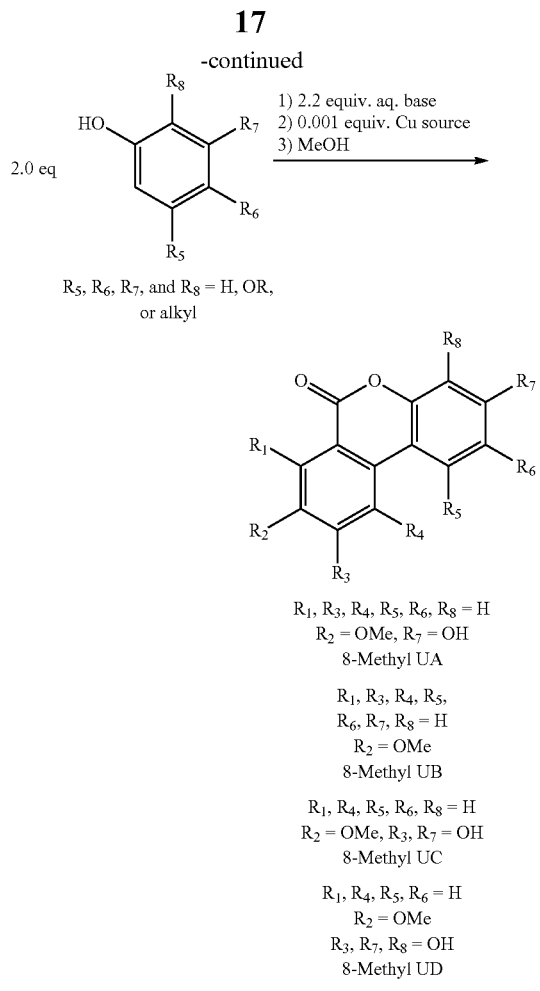

$R_5$, $R_6$, $R_7$, and $R_8$ = H, OR, or alkyl $R_1$, $R_3$, $R_4$, $R_5$, $R_6$, $R_8$ = H
$R_2$ = OMe, $R_7$ = OH
8-Methyl UA $R_1$, $R_3$, $R_4$, $R_5$, $R_6$, $R_7$, $R_8$ = H
$R_2$ = OMe
8-Methyl UB $R_1$, $R_4$, $R_5$, $R_6$, $R_8$ = H
$R_2$ = OMe, $R_3$, $R_7$ = OH
8-Methyl UC $R_1$, $R_4$, $R_5$, $R_6$ = H
$R_2$ = OMe
$R_3$, $R_7$, $R_8$ = OH
8-Methyl UD Remarkably, contrary to literature precedent, it was subsequently discovered that copper levels could be reduced by at least 2000-fold compared to a number of similar reactions reported in the literature, and reduced by at least 600-fold compared to the lowest copper level reported in the literature for similar reactions. The optimized copper loading was 75 μg $CuSO_4$ per gram carboxylic acid substrate, or 0.1 mol %. Moreover, the levels of copper contamination found in the isolated products were <1 ppm, without resorting to column chromatography or other expensive purification techniques.

As shown in Scheme 1, variability will be possible in both coupling partners, giving rise to an extensive scope of urolithin compounds and analogs that can be produced by the present method. The carboxylic acid coupling partner should perform well whether Cl, Br, or I is the X moiety. One or more of $R_1$-$R_4$ can be H, OH or OR, particularly OMe, without negatively impacting the reaction. As for the phenol coupling partner, $R_5$-$R_8$ can each be H, OH, or OR, particularly OMe, without negatively impacting the reaction. Although aqueous sodium hydroxide (NaOH) is a preferred alkaline solution for the reaction solvent, other bases can be used, such as, for example, LiOH, NaOH, KOH, CsOH, $Na_2CO_3$, $CaCO_3$, or $Cs_2CO_3$.

Scheme 2 shows a specific example of the copper-catalyzed coupling as applied to the synthesis of a urolithin A precursor/analog, 8-methyl urolithin A (abbreviated herein 8-methyl UA). A solution of the starting materials 2-bromo-5-methoxy-benzoic acid and resorcinol in dilute sodium hydroxide reacts in the presence of a catalytic amount of copper sulfate to produce the corresponding biaryl compound 8-methyl urolithin A by elimination of hydrogen bromide and water at 70-100° C. The poorly soluble product readily precipitates from the reaction mixture even at elevated temperature and is isolated by filtration. No additional purification is required. After drying the compound is used in the downstream process as it is received. The desired product, 8-methyl urolithin A, was obtained in 76% yield.

Scheme 2 - Formation of 8-methyl urolithin A by Ullmann Coupling

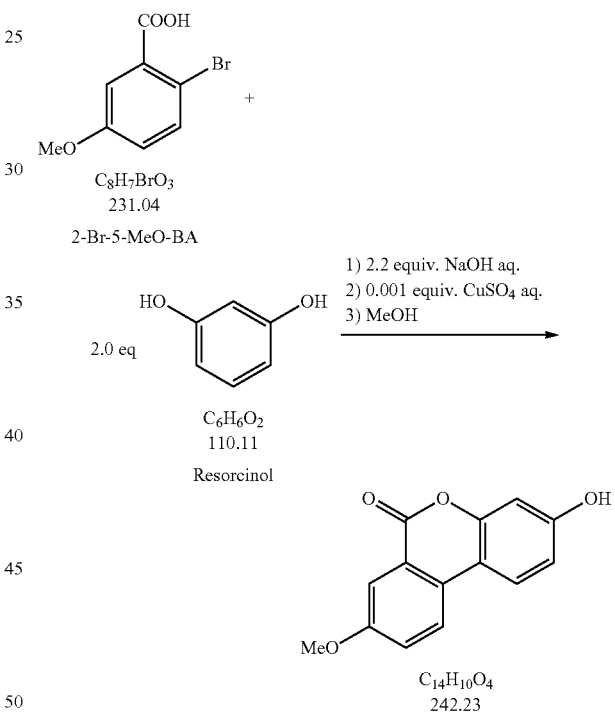

As shown in Table 1 and Table 2, all starting materials and reagents are commercially available and meet all necessary parameters for use in the manufacturing process.

TABLE 1

Raw Materials & Quantities Used
The following materials are required to prepare 45-47 g of 8-methyl urolithin A.[a]

| Material | Formula | MW | kg/L | Amount | mmol | equiv. | CAS |
|---|---|---|---|---|---|---|---|
| 2-Bromo-5-methoxy-benzoic acid | $C_8H_7BrO_3$ | 231.04 | — | 56.76 g | 250 | — | 22921-68-2 |
| Resorcinol | $C_6H_6O_2$ | 110.11 | — | 55.06 g | 500 | 2.0 | 108-46-3 |
| 50% Sodium Hydroxide | NaOH | 40.01 | 1.525 | 44.00 g | 550 | 2.2 | 1310-73-2 |
| Water | $H_2O$ | 18.02 | 1.000 | 355 mL | — | — | 7732-18-5 |

TABLE 1-continued

Raw Materials & Quantities Used
The following materials are required to prepare 45-47 g of 8-methyl urolithin A.[a]

| Material | Formula | MW | kg/L | Amount | mmol | equiv. | CAS |
|---|---|---|---|---|---|---|---|
| Copper sulfate pentahydrate | $CuSO_4 \cdot 5H_2O$ | 249.68 | — | 62.4 mg | 0.25 | 0.001 | 7758-99-8 |
| Water | $H_2O$ | 18.02 | 1.000 | 500 mL | — | — | 7732-18-5 |
| Methanol | $CH_4O$ | 32.04 | 0.792 | 250 mL | — | — | 67-56-1 |

[a]All intermediates used on an "as is"-base, i.e. without correction for potency.

TABLE 2

Specifications of Raw Materials

| Material | Assay[a] | Used in Batch |
|---|---|---|
| 2-Bromo-5-methoxy-benzoic acid | 98% 99.04%[b] | LB1659 LB1669, LB1670 |
| Resorcinol | 99.9% | LB1659, LB1669, LB1670 |
| 50% Sodium Hydroxide | ≥98.5%[c] 49.77% | LB1659 LB1669, LB1670 |
| Water | — | LB1659, LB1669, LB1670 |
| Copper sulfate pentahydrate | 100.2% | LB1659, LB1669, LB1670 |
| Methanol | 99.9% | LB1659, LB1669, LB1670 |

[a]Assay according to CoA.
[b]area % (HPLC).
[c]Assay of neat sodium hydroxide.

Process Details

The following process description is based on batches LB1659, LB1669, and LB1670. Yields and analytical data are derived from these batches and a series of similar laboratory batches.

1. Charge the flask with 2-Bromo-5-methoxy benzoic acid (56.8 g, 250 mmol), 2.0 equivalents (equiv.) of Resorcinol (55.1 g, 500 mmol), 6.25 vol. of water (375 mL) and start stirring.
2. Add 2.2 equiv. of 50% sodium hydroxide (44.0 g, 550 mmol) with agitation at 20-45° C.
Note: The addition of sodium hydroxide is slightly exothermic.
3. Render the flask inert and warm the reaction mass under nitrogen to 40-45° C.
4. Add neat 0.001 equiv. of copper sulfate pentahydrate (62.4 mg, 0.25 mmol) to the reaction mixture.
5. Heat the mixture to 70-90° C.
6. Continue agitation for at least 3 hours until HPLC indicates conversion of 2-Bromo-5-methoxy benzoic acid to 8-methyl urolithin A is greater than or equal to 97.0%.
7. Cool the reaction mixture to 20-25° C.
8. Continue agitation for at least 1 hour at ambient temperature.
9. Collect the precipitate by filtration.
10. Rinse the filter cake subsequently with 3.5-7 vol. of water (200-400 mL) and 1.7-3.4 vol. of methanol (100-200 mL).
11. Dry the damp product under reduced pressure at 40° C.
8-methyl urolithin A is received as an off-white to pale yellow solid.

TABLE 3

Yields

| | Batch: | | |
|---|---|---|---|
| | LB1659 | LB1669 | LB1670 |
| Input | | | |
| 2-Bromo-5-methoxy benzoic acid | 56.76 g | 57.76 g | 56.76 g |
| Output | | | |
| 8-methyl UA | 46.19 g | 45.94 g | 44.06 g |
| Yield "as is" | 76% | 76% | 74% |

Key in-Process Controls (IPC)

The following key in-process controls were recorded:

| Step | Test | Method | LB1659 | LB1669 | LB1670 | Limit[a] |
|---|---|---|---|---|---|---|
| 5 | HPLC | | 97.7% | 97.7% | 97.5% | min. 97.0% |

[a] The given limits are tentative limits defined on the basis of the results achieved in the described batches.

Analytical Results

The following analytical results were determined for the three batches.

| Test | Specification | LB1659 | LB1669 | LB1670 |
|---|---|---|---|---|
| Appearance | off-white to yellow, green or purple solid | pale yellow solid | pale yellow solid | pale yellow solid |
| Identity | | | | |
| by HPLC | conforms to reference | conforms | conforms | conforms |
| by $^1H$ NMR | conforms to structure | conforms | conforms | conforms |
| Assay [% wt.] | | n.d. | 99.9% | 99.9% |
| Purity [area %] | ≥98.0% | 99.5% | 99.5% | 99.5% |
| Water Content | | n.d. | 0.15% | n.d. |

The optimized amount of copper catalyst is 0.001 equiv. The color of the intermediate 8-methyl urolithin A was darker (purple) when a higher catalyst loading of 0.1 equiv. was employed, whereas it is pale yellow with the current procedure. Even though the catalyst load was reduced significantly this did not have a negative impact on the dedicated reaction time, the conversion rate or the purity of the product.

TABLE 4

Screening of Reaction Conditions

| Exp. | Scale | Yield | Purity | Comment |
|---|---|---|---|---|
| LB1631 | 250 mmol | 63% | 98.4% | 0.1 equiv. $CuSO_4$ |
| LB1640 | 40 mmol | 74% | 99.2% | 0.02 equiv. $CuSO_4$ |
| LB1647 | 40 mmol | 72% | 99.5% | 0.001 equiv. $CuSO_4$ |
| LB1649 | 40 mmol | 55% | 98.9% | 0.001 equiv. $CuSO_4$, 1.25 equiv. Resorcinol |
| LB1653 | 250 mmol | 76% | 99.5% | 0.001 equiv. $CuSO_4$, 2 equiv. Resorcinol |

The product from each experiment was thoroughly characterized by $^1$H NMR and QNMR.

Figure 2:
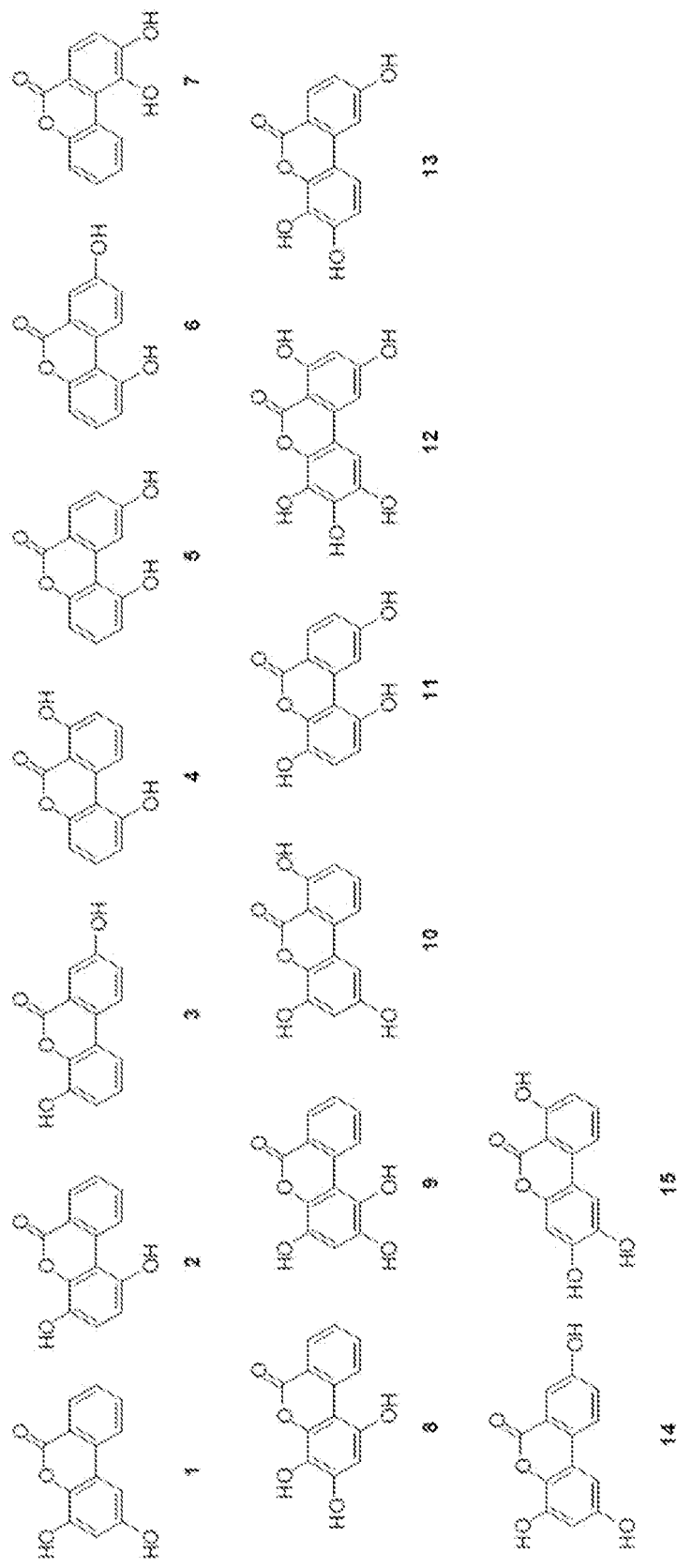
FIG. 2 shows the chemical structures of exemplary urolithin analogues that may be prepared by a method of the present invention.

The surprising discovery that the loading of the copper catalyst could be decreased more than 1000-fold without impacting the reaction time or yield of the product is predicted to be applicable to urolithin precursors, intermediates, and analogs, for example those shown in Scheme 1 and FIGS. 1 and 2). Furthermore, it is expected that alternate copper sources known to work in Ullmann and Hurtley reactions are within the scope of this invention. A variety of copper sources are commonly used and could, subject to normal experimentation, provide the same or improved results. Such copper sources include activated copper powder, copper-bronze couple, $CuSO_4$ (hydrate or anhydrous), $Cu(acac)_2$, CuCl, $CuCl_2$, CuBr, $CuBr_2$, CuI, $Cu_2O$, CuO, CuOTf, and CuCN.

Example 2

Demethylation of Ullmann Coupling Product

To prepare the desired urolithin compounds, it is necessary to remove one or more methyl groups used to protect the hydroxyl(s) of the coupling partners in the first step described above. Such reactions can be unpredictable and often require harsh conditions. One reagent frequently used in this reaction is $BBr_3$, a highly toxic and reactive reagent that violently decomposes in contact with water to form HBr gas, itself a toxic and corrosive strong acid. These drawbacks make $BBr_3$ relatively costly and difficult to purchase and ship in the large quantities required for process-scale work. For these reasons an alternative was sought. Remarkably, the preparation of compound urolithin A from mono-methyl ether 8-methyl urolithin A was accomplished by ether deprotection with aluminum chloride ($AlCl_3$) in an efficient and advantageous manner. Urolithin A was provided in improved yield and under less costly, safer, and simpler conditions than in known protocols using $BBr_3$.

Aluminum trichloride ($AlCl_3$) is a powerful Lewis acid frequently used in electrophilic aromatic chlorination reactions and Freidel-Crafts acylations. Similar chemical reagents include $FeCl_3$ and $AlBr_3$. $AlCl_3$ is advantageous for its low cost and ease of use (it is a free-flowing white powder, as opposed to $BBr_3$, which is a highly reactive liquid that is unsafe to handle neat).

A suspension of the starting material 8-methyl urolithin A and 5 equiv. of aluminum chloride in toluene was heated to 90-100° C. After cleavage of the methyl ether the mixture was quenched by addition of water and the product precipitated. To enable the required polish filtration and a final purification, two additional process steps were required. The raw product was dissolved in DMSO and the solution was cleared by filtration. By addition of water the product precipitated again. It was found that the crude product could then be easily purified by trituration in acetic acid at reflux for several hours. This trituration, unknown in previous syntheses of urolithins, proved highly effective at removing impurities. Furthermore, after the trituration the filtration of the product and the rinse of the filter cake proceeded at a much faster rate. After drying the filter cake and delumping, the final product urolithin A was obtained as an off-white to yellow free flowing solid.

Alternatively, the demethylation could be performed using another strong Lewis acid such as $AlBr_3$, $BeCl_2$, $FeCl_3$, or $SiCl_4$. A $C_2$-$C_{24}$ thiol such as ethanethiol or dodecanethiol may also be added; such thiols may be used as the solvent. In many cases, a deprotonated $C_2$-$C_{24}$ thiol, e.g., sodium ethanethiolate (NaSEt), may be used as the sole demethylation reagent. An especially useful system is a mixture of anhydrous ethanethiol and $AlCl_3$. Also, since methylene groups are often used to protect ortho dihydroxybenzenes (and they can be deprotected using the same conditions as methyl ethers), they could be used in preparing a number of the urolithin analogs shown in FIG. 2 having adjacent hydroxyl functionality, for example, compounds 7, 8, 9, 12, and 13. However, $AlCl_3$, $AlCl_3$/EtSH, or NaSEt have been used to remove two or more methyl groups in anisole-, resveratrol-, and trimethoxybenzene-type systems, so intermediates bearing multiple methoxy groups would provide a viable route to such compounds as 7, 8, 9, 12, and 13 of FIG. 2. A general approach is shown in Scheme 3.

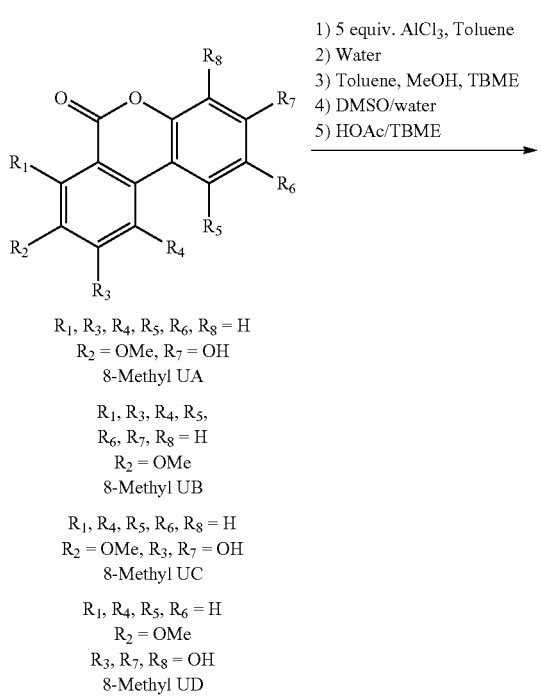

Scheme 3 - General Reaction Scheme 1) 5 equiv. $AlCl_3$, Toluene
2) Water
3) Toluene, MeOH, TBME
4) DMSO/water
5) HOAc/TBME $R_1$, $R_3$, $R_4$, $R_5$, $R_6$, $R_8$ = H
$R_2$ = OMe, $R_7$ = OH
8-Methyl UA $R_1$, $R_3$, $R_4$, $R_5$,
$R_6$, $R_7$, $R_8$ = H
$R_2$ = OMe
8-Methyl UB $R_1$, $R_4$, $R_5$, $R_6$, $R_8$ = H
$R_2$ = OMe, $R_3$, $R_7$ = OH
8-Methyl UC $R_1$, $R_4$, $R_5$, $R_6$ = H
$R_2$ = OMe
$R_3$, $R_7$, $R_8$ = OH
8-Methyl UD -continued

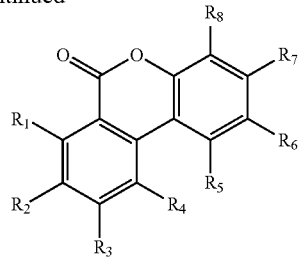

R$_1$, R$_3$, R$_4$, R$_5$, R$_6$, R$_8$ = H
R$_2$, R$_7$ = OH
Urolithin A (UA)

R$_1$, R$_3$, R$_4$, R$_5$,
R$_6$, R$_7$, R$_8$ = H
R$_2$ = OH
Urolithin B (UB)

R$_1$, R$_4$, R$_5$, R$_6$, R$_8$ = H
R$_2$, R$_3$, R$_7$ = OH
Urolithin C (UC)

R$_1$, R$_4$, R$_5$, R$_6$ = H
R$_2$, R$_3$, R$_7$, R$_8$ = OH
Urolithin D (UD)

A number of solvents are compatible with the use of AlCl$_3$ or similar Lewis acids. Although toluene is advantageous for its low environmental impact and low toxicity, dichloromethane, dichloroethane, chloroform, carbon tetrachloride, chlorobenzene, diethyl ether, 1,4-dioxane, tert-butyl methyl ether (TBME), tetrahydrofuran (THF), N,N-dimethylformamide (DMF), N-methylpyrrolidone (NMP), diglyme, nitromethane, 1,2-dimethoxyethane (DME), pyridine, ethyl acetate, acetone, acetonitrile, benzene, o-xylene, m-xylene, p-xylene, xylenes, hexanes, cyclohexane, heptane, octane, nonane, and decane, and mixtures thereof, are all viable alternatives. As mentioned above, one or more C$_2$-C$_{24}$ thiols can be added to this list as additives, co-solvents, or reagents. In contrast, fewer solvents can be used with BBr$_3$ because ethers and protic solvents (e.g., alcohols) react violently with BBr$_3$.

Other additives such as LiCl, NaI, tetrabutylammonium iodide (Bu$_4$NI), NaOMe, and trimethylamine hydrochloride, can accelerate the action of AlCl$_3$, BeCl$_2$, FeCl$_3$, and SiCl$_4$ in aromatic ether deprotections.

The usefulness of this deprotection method is highlighted by the process-scale preparation of urolithin A from the intermediate 8-methyl urolithin A, the preparation of which is described in the previous Example. Scheme 4 shows a summary of the transformation and the steps involved.

Scheme 4 - Formation of Urolithin A by Demethylation Reaction

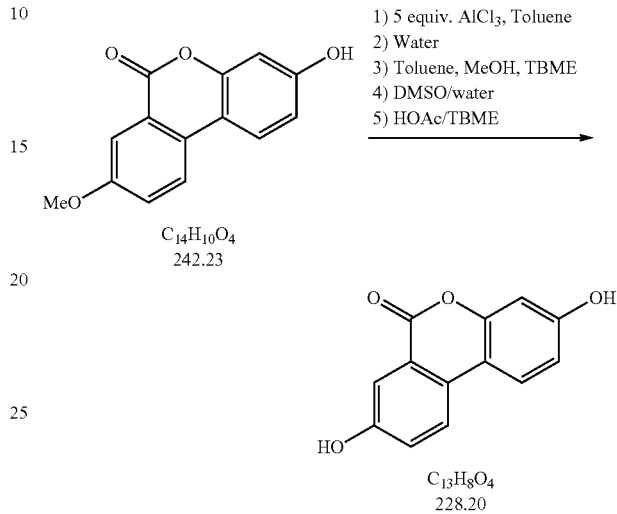

There are several advantageous aspects of this method. Although the use of AlCl$_3$ for demethylation reactions is often associated with the need for elevated temperatures and a high-boiling solvent—for example, refluxing chlorobenzene at 131° C.—it was found that 90-100° C. in toluene was sufficient. Toluene is a more environmentally-friendly solvent than chlorobenzene. Furthermore, lower temperatures are preferable for process-scale work for several reasons, including safety and energy costs. The reaction time was 1-2 h, whereas reaction times of as much as 4 days were previously reported with similar substrates. The yield is also substantially improved. Reported yields of 30-60% with similar substrates (37% with a urolithin compound) were improved to 87-89% using the present, optimized process.

TABLE 5

Identity and Quantities of Raw Materials
The following materials are required to prepare 38-40 g of urolithin A.[a]

| Material | Formula | MW | kg/L | Amount | | mmol | equiv. | CAS # |
|---|---|---|---|---|---|---|---|---|
| Part 1: | | | | | | | | |
| 8-methyl UA | C$_{14}$H$_{10}$O$_4$ | 242.23 | — | 48.4 | g | 200 | — | — |
| Aluminum chloride | AlCl$_3$ | 133.34 | — | 133.3 | g | 1000 | 5.0 | 7446-70-0 |
| Toluene | C$_7$H$_8$ | 92.14 | 0.87 | 500 | mL | — | — | 108-88-3 |
| Water | H$_2$O | 18.02 | 1.00 | 900 | mL | — | — | 7732-18-5 |
| Methanol | CH$_4$O | 32.04 | 0.79 | 200 | mL | — | — | 67-56-1 |
| Part 2: | | | | | | | | |
| DMSO | C$_2$H$_6$OS | 78.13 | 1.10 | 200 | mL | — | — | 67-68-5 |
| Water | H$_2$O | 18.02 | 1.00 | 800 | mL | — | — | 7732-18-5 |
| Part 3: | | | | | | | | |
| Acetic acid | C$_2$H$_4$O$_2$ | 60.05 | 1.05 | 656 | mL | — | — | 64-19-7 |
| tert-Butyl methyl ether | C$_5$H$_{12}$O | 88.15 | 0.74 | 200 | mL | — | — | 1634-04-4 |

[a]All intermediates used on an "as is"-base, i.e. without correction for potency.

TABLE 6

Specifications of Raw Materials

| Material | Assay[a] | ID | Used in Batch |
|---|---|---|---|
| 8-methyl UA | — | LB1651/1659 | LB1671 |
| | | LB1669 | LB1681 |
| | | LB1670 | LB1683 |
| Aluminum chloride | 99.0% | #215529 | LB1671 |
| | 99.6% | IT-5714 | LB1681/LB1683 |
| Toluene | 99.9% | IT-5291 | LB1671/LB1681/LB1683 |
| Water, deion. | — | — | LB1671/LB1681/LB1683 |
| Methanol | 99.9% | IT-5634 | LB1671/LB1681/LB1683 |
| DMSO | 99.9%[b] | IT-4687 | LB1671/LB1681/LB1683 |
| Acetic acid | 99.9% | IT-5515 | LB1671/LB1681/LB1683 |
| TBME | 99.97% | IT-5562 | LB1671/LB1681/LB1683 |

[a]Assay according to CofA;
[b]AP = area % (HPLC).

Process Details

The following process description is based on batches LB1671, LB1681 and LB1683. Yields and analytical data are derived from these batches and a series of similar laboratory batches.

Part 1: Ether Cleavage
1. Charge the flask with 8-methyl urolithin A (48.4 g, 200 mmol), 5 equiv. Aluminum chloride (133.3 g, 1000 mmol), 10 vol. Toluene (500 mL) and start stirring vigorously.
Note: Heavy, sticking suspension. Agitate vigorously.
2. Render the reaction mixture inert with nitrogen.
3. Heat the mixture to 90-100° C. within at least 40 min.
4. Continue agitation for 1-2 hours at 90-100° C.
5. Stop heating and allow the reaction mixture to cool to 50-80° C.
6. Add 10-15 vol. of water (500-750 mL) continuously with vigorous stirring.
Note: Addition/hydrolysis is exothermic. Reflux may be reached. Start addition slowly.
7. Continue agitation between 20-100° C. for at least 2 hours with cooling until all cakes are released from the glass.
8. Adjust the temperature of the suspension to 20-40° C.
9. Collect the precipitate by filtration.
10. Rinse the filter cake with 8.0-8.3 vol. of water (385-400 mL) in portions.
11. Rinse the filter cake with 4.0-4.1 vol. of methanol (195-200 mL).
12. Dry the wet cake in a flow of dry nitrogen or under reduced pressure at max. 60° C. until LOD (Loss On Drying; 120° C., 20 min)≤50% wt.

Part 2: Polish Filtration
13. Charge the flask with the damp product from step 12.
14. Add 4.0-4.1 vol. of DMSO (195-200 mL) and start agitation.
15. Continue agitation until complete dissolution achieved but at least for 60 min at 20-25° C.
16. Filter the solution at ambient temperature.
Note: Small amount of residue expected. Brown filtrate.
17. Charge another flask with 12.0-12.4 vol. of filtered water (580-600 mL) and initiate agitation.
18. Add the DMSO solution from step 16 slowly to the water over at least one hour at 20-25° C.
19. Continue agitation of the received suspension for min. 30 min at 20-25° C.
20. Collect the precipitate by filtration.
21. Rinse the filter cake with 4.0-4.1 vol. of filtered water (195-200 mL) in portions.
22. Dry the damp product in a flow off dry nitrogen or under reduced pressure at max. 60° C. until LOD (120° C., 60 min)≤80% wt.

Part 3: Recrystallization
23. Charge a clean flask with the crude product from step 22.
24. Add 9.4 vol. of filtered acetic acid (456 mL) and start stirring.
25. Heat the suspension to reflux (boiling point of acetic acid=116-118° C.) with moderate agitation.
26. Continue agitation for 4-5 hours at reflux.
27. Cool the slurry to 20-40° C.
28. Collect the precipitate by filtration.
29. Rinse the filter cake with 4.0-4.1 vol. of filtered acetic acid (195-200 mL) in portions.
30. Rinse the filter cake with 4.0-4.1 vol. of filtered TBME (195-200 mL) in portions.
31. Dry the damp product under reduced pressure at max. 70° C. until LOD (120° C., 20 min)≤0.5% wt. and residual solvents by GC below ICH limits.
Note: Limit for toluene max. 890 ppm, TBME max. 5000 ppm, acetic acid 5000 ppm.

TABLE 7

Yields

| | Batch: | | |
|---|---|---|---|
| | LB1671 | LB1681 | LB1683 |
| Input | | | |
| 8-methyl UA | 48.4 g | 36.3 g | 36.3 g |
| Output | | | |
| Urolithin A | ½ · (38.4 g)[a] | 30.0 g | 30.4 g |
| Yield "as is" | 84% | 88% | 89% |

[b] Batch LB1671 was separated into two parts of the same size after step 16. The first part was worked up and isolated as described herein. 19.2 g of urolithin A were isolated. The "output" and the yield in this table are corrected accordingly. The second part of batch LB1671 was used for the preparation of the reference standard LB1675.

TABLE 8

Key in-process controls (IPC)
The following key in-process controls were recorded:

| Step | Test | Method[a] | LB1671 | LB1681 | LB1683 | Tentative[c] Limit |
|---|---|---|---|---|---|---|
| 5 | conversion | HPLC | 99.5% [1.0 h] | 99.9% [1.5 h] | 99.7% [1.7 h] | [d] |
| 12 | LOD | 120° C., 20 min | n. dtd.[b] | 46.6% wt | 10.1% wt | max. 50% wt. |
| | purity | HPLC | 94.5% | 99.3% | 99.5% | min. 95% |
| 22 | LOD | 120° C., 60 min | n. dtd. | 80.0% wt | 79.4% wt | max. 80% wt. |

TABLE 8-continued

Key in-process controls (IPC)
The following key in-process controls were recorded:

| Step | Test | Method[a] | LB1671 | LB1681 | LB1683 | Tentative[c] Limit |
|---|---|---|---|---|---|---|
| 31 | LOD | 120° C., 20 min | n. dtd. | n. dtd. | 0.3% wt | max. 0.5% wt. |
|  | GC | Toluene | n. dtd. | n. dtd. | n. dtd. | max. 890 ppm |
|  |  | Methanol | n. dtd. | n. dtd. | n. dtd. | max. 3000 ppm |
|  |  | TBME | n. dtd. | n. dtd. | n. dtd. | max. 5000 ppm |
|  |  | DMSO | n. dtd. | n. dtd. | n. dtd. | max. 5000 ppm |
|  |  | RLM_4_GC HOAc | n. dtd. | n. dtd. | n. dtd. | max. 5000 ppm |

[a]Detailed descriptions of the test methods are attached to this document or available on request.
[b]Not determined.
[c]The given limits are tentative limits defined on the basis of the results achieved in the described batches.
[d]In all experiments the conversion was finished after 1 hour and no major impurities were generated over 2 hours. Therefore the reaction time was set to 1-2 hours for the intended production campaign.

TABLE 9

Analytical Results

The following analytical results were determined for the three batches:

| Test | Specification | LB1671 | LB1681 | LB1683 |
|---|---|---|---|---|
| Appearance | off-white to yellow solid | pale yellow solid | pale yellow solid | yellow solid |
| Identity | conforms | conforms ($^1$H NMR) | conforms ($^1$H NMR) | conforms ($^1$H NMR) |
| Assay | report | 103% (QNMR) | 98% (HPLC) | 97% (HPLC) |
| Purity | NLT 97% | 99.7% | 99.9% | 99.9% |
| impurities | report all >0.1% | RRT 1.05:0.1% | none | none |
| Water Content | report | n.dtd. | n.dtd. | n.dtd. |

Residual Solvents

| Toluene | ≤890 ppm (w/w) | n.dtd. | 9 ppm | n.d. |
| Methanol | ≤3000 ppm (w/w) | n.dtd. | n.d. | n.d. |
| TBME | ≤5000 ppm (w/w) | n.dtd. | 18 ppm | n.d. |
| HOAc | ≤5000 ppm (w/w) | n.dtd. | 1341 ppm | 1854 ppm |
| DMSO | ≤5000 ppm (w/w) | n.dtd. | 73 ppm | 55 ppm |
| ROI | report | n.dtd. | n.dtd. | n.dtd. |
| Heavy Metals | NMT 20 ppm | n.dtd. | n.dtd. | n.dtd. |
| Copper | report | n.dtd. | <1 ppm | <1 ppm |
| Aluminum | report | n.dtd. | 7 ± 1 ppm | 16 ± 1 ppm |

TABLE 10

Specifications

Specifications for product urolithin A:

| Test | Method | Specification |
|---|---|---|
| Appearance | APP_1 | off-white to yellow solid |
| Identity by IR | IR_ATR | conforms to reference |
| Assay by HPLC |  | report result |
| Purity by HPLC |  | NLT 97 area %[a] |
| Impurities |  | report all >0.1 area % |
| Water Content | KF_1 | report result |
| Residual Solvents | GC | according to ICH guideline |
| Toluene |  | NMT 890 ppm (w/w) |
| Methanol |  | NMT 3000 ppm (w/w) |
| TBME |  | NMT 5000 ppm (w/w) |
| Acetic acid | RLM_4_GC | NMT 5000 ppm (w/w) |
| DMSO |  | NMT 5000 ppm (w/w) |
| Residue on Ignition | <USP 281> | report result |
| Heavy Metals | <USP 231> | NMT 20 ppm |
| Copper |  | report result |
| Aluminum |  | report result |

TABLE 10-continued

Specifications

| Microbial Enumeration Test |  | <USP 61> |
| Total aerobic microbial count |  | NMT 1000 CFU/g |
| Total combined yeast & mould count |  | NMT 100 CFU/g |

[a]NLT no less than;
NMT no more than.

The demethylation of the ether can be accomplished in DCM with 3 equiv. of boron tribromide. While workable for a laboratory-scale synthesis, it is unacceptable for process work. The disadvantages of the procedure include the relatively poor availability of large quantities of boron tribromide, its long delivery time, its toxicity and the relatively high cost. In the current procedure boron tribromide is replaced by aluminum trichloride, which is readily available in large quantities at a lower cost.

The damp raw product is used in the polish filtration step in DMSO and the final trituration step in acetic acid. After the trituration in acetic acid both the filtration and the rinse of the filter cake are improved significantly.

Notably, the process delivers the final product urolithin A with excellent purity as evidenced by the low levels of heavy metals: <1 ppm copper and <17 ppm aluminum.

Example 3

Preparation of Urolithin B

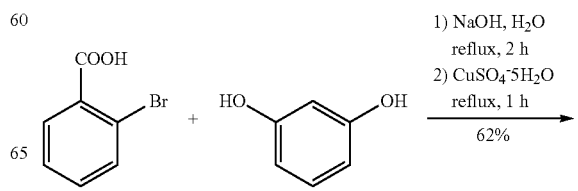

-continued

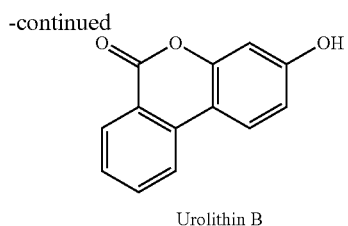

Urolithin B

Urolithin B was prepared in one step by coupling resorcinol and 2-bromobenzoic acid following the procedure for the preparation of Urolithin A. The pure compound was obtained as a off-white powder with a yield of 61.6%.

Example 4

Preparation of 8-(benzyloxy)-3-hydroxy-6H-benzo[c]chromen-6-one (16)

8-(benzyloxy)-3-hydroxy-6H-benzo[c]chromen-6-one (16) was prepared as follows:

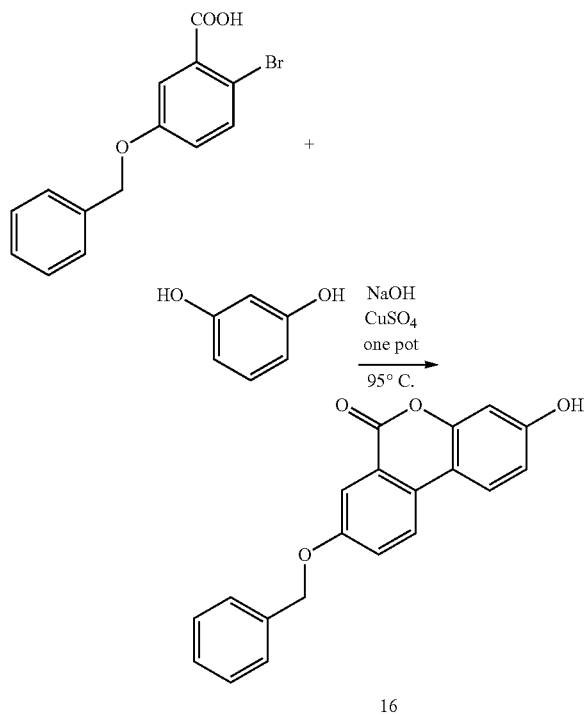

16

Compound 16 was obtained with a yield of 60%.

Example 5

Large-Scale Process for Preparation of Urolithin A

The process described in Example 2 was successfully scaled up with inputs of 40.0 kg 2-Br-5-MeO-benzoic acid and 38.8 kg resorcinol to deliver 24.14 kg of urolithin A.

Step 1: Ullmann Coupling

Introduction.

The formation of methyl ester 8-methyl urolithin A in step 1 represents a tandem Ullmann coupling/esterification reaction. In the Ullmann step 2-bromo-5-methoxy benzoic acid is activated with a catalytic amount of copper and the activated species is coupled with Resorcinol. After release of the catalyst and hydrogen bromide intramolecular formation of the cyclic ester in 8-methyl urolithin A takes place by release of one equivalent of water. The focus of this Example is on the scale-up results.

Production: Batch RR01L108A0.

The production under GMP conditions was accomplished in a single batch. The production scale was 40.0 kg of commercially available 2-Bromo-5-methoxy benzoic acid. The standard equipment used in the Miniplant were a 450 L Hastelloy reactor, 1000 L stainless steel tank, 850 L stainless steel tank, 150 L stainless steel filter, QuadroComil, 100 mL brown-glass bottle and a stainless steel vacuum tray dryer.

The solution of the catalyst was prepared by dissolving copper sulfate pentahydrate (4.4 g, 0.02 mol) in purified water (28 mL) at ambient temperature. The solution was stored in a glass bottle until use. The reactor was charged with 2-Bromo-5-methoxy benzoic acid (40.0 kg, 173.1 mol), 2.0 equiv. of resorcinol (38.8 kg, 352.4 mol), and 6.6 vol. of purified water (265 L). Agitation was started and 2.2 equiv. of 50% caustic soda (31.0 kg, 387.6 mol) were added at a rate keeping the bulk temperature bellow 40° C. (30 min required). Stirring was continued for 5 min at 25° C. until a clear solution was obtained. The aqueous copper sulfate solution prepared previously was added at 25° C. The reaction mixture was heated to 70° C. within 75 min. The reaction mixture became very thick and viscous. The speed of stirring and mixing was significantly reduced. Therefore the mixture was diluted with additional 1.3 vol. of purified water (50 L). Stirring at 70-90° C. was continued until In Process Control by HPLC indicated conversion of 2-Bromo-5-methoxy benzoic acid to 8-methyl urolithin A ≥97% (5 hours required). The reaction mixture was cooled from 89° C. to 25° C. within 20 min and agitation was continued overnight (14 hours). The product was collected by filtration (48 hours required) and the filter cake was rinsed on the filter subsequently with 3.5 vol. of purified water (141 L, 60 hours required) and 1.8 vol. of methanol (56.0 kg, 71 L, 40 hours required). After combination of the mother liquor with the rinse solution the mixture was checked for residual product and discarded. The filter cake was dried in a flow of dry nitrogen and under reduced pressure at 30-50° C. for 2 days until LOD=0.3% wt. Finally de-lumping of the material was accomplished in a QuadroComil using a 1.9 mm sieve.

The product was received in a yield of 75% corresponding to 31.3 kg of 8-methyl urolithin A.

TABLE 11

Analytical results for 8-methyl urolithin A from GMP-batch RR01L108A0 and PLPD (Preliminary Laboratory Process Description) experiments

| Test | Specification | RR01L108A0 | PLPD experiments |
|---|---|---|---|
| Appearance | off-white to yellow green or purple solid | yellowish to beige solid | pale yellow solid |
| Identity by HPLC | conforms to reference | conforms | conforms |
| Identity by $^1$H NMR | conforms to structure | conforms | conforms |
| Assay by QNMR | report result | 98.6% wt. | 99.9% wt. |
| Purity by HPLC | ≥98.0 area % | 99.5% | 99.5% |
| Water by Karl Fischer | report result | 0.13% wt. | 0.15% wt. |

TABLE 12

Key raw materials for the production of 8-methyl urolithin A in batch RR01L108A0; Summary of process results

| Compound | CAS-No. | Purity[a] | IT-no. |
|---|---|---|---|
| 2-Bromo-5-Methoxy Benzoic Acid | 22921-68-2 | 99.04% | 5700 |
| Resorcinol | 108-46-3 | 99.9% | 5682 |
| 50% Caustic Soda | 1310-73-2 | 49.77% | 5652 |
| Purified Water | 7732-18-5 | n.a. | n.a. |
| Copper (II) Sulfate Pentahydrate | 7758-99-8 | 100.2% | 5683 |
| Methanol | 67-56-1 | 99.9% | 5634 |
| Water for Injection | 7732-18-5 | n.a. | 4728 |

[a]According to CoA or other analytical information.

| | Input | | Output | | Yield |
|---|---|---|---|---|---|
| Batch | kg | 2-Br-5-MeO-BA | kg | HI | corr. |
| RR01L108A0 | 40.00 | RRIT-5700 | 31.28 | 99.5% | 75% |

The product 8-methyl urolithin A from batch RR01L108A0 was successfully released for the preparation of clinical trial material.

Step 2: Ether Cleavage

Introduction.

The release of the diol, urolithin A, from the methyl ether, 8-methyl urolithin A, in step 2 represents an ether cleavage under acidic conditions in the presence of aluminum chloride. The methyl ether in 8-methyl urolithin A is activated by an excess of Lewis acid (aluminum chloride) and the activated species is finally hydrolyzed, leading to the alcohol 8-methyl urolithin A, hydrochloric acid and aluminum hydroxide. The crude product is dissolved in DMSO for a polish filtration and subsequently precipitated from the DMSO-solution by addition of water. After filtration the raw product is triturated with acetic acid at reflux to remove last impurities and to get the product in a solid-form that enables better filtration than the raw product from DMSO/water. The focus of this Example is on the scale-up results. Detailed descriptions of the GMP batches RR01L111A0, RR02L111A0, RR03L111A0 and RR03L111A1 are provided.

The production under GMP conditions was accomplished in 4 batches total. In the first two batches RR01L111A0 and RR02L111A0 intermediate 8-methyl urolithin A from step 1 was converted to the crude product urolithin A by cleavage of the methyl ether, hydrolysis with water and filtration. The production scale was 15.25 kg per batch of 8-methyl urolithin A prepared in RR01L108A0. The standard equipment used in the Miniplant was a 600 L glass-lined reactor, 800 L glass-lined container, stainless steel centrifuge and a 1000 L stainless steel tank.

The two crude products were combined for the polish filtration of the DMSO solution in batch RR03L111A0. The production scale was 88.86 kg of damp urolithin A prepared in batches RR01L111A0 and RR02L111A0. The standard equipment used in the Miniplant were a 600 L glass-lined reactor, 1000 L glass-lined reactor, Begerow filter cartridge holder, three stainless steel filters, two 1000 L stainless steel tank, a 800 L stainless steel tank, particle filter cartridge and a QuadroComil (sieve mill).

Batch RR01L111A0.

The reactor was charged with 8-methyl urolithin A (15.25 kg, 63.0 mol), 5.0 equiv. of aluminum chloride (42.0 kg, 315.0 mol) and 10.3 vol. of toluene (137.0 kg, 157 L). Agitation was started and the reaction mixture was heated to 90° C. within 75 min. Stirring was continued for 2 hours at 90-96° C. After cooling the reaction mass to 53° C. over 25 min., 0.6 vol. of water for injection (9.4 L) followed by 10.8 vol. of purified water (164 L) were added within 2 hours carefully at 48-53° C. Agitation was continued for 2 hours at 39-48° C. to remove all tipping from the reactor wall before the mixture was cooled to 37° C. in 15 min. The product was collected by filtration at 23-37° C. (70 min required) and the filter cake was rinsed with 4.2 vol. of methanol (50.0 kg, 63 L, 30 min required). After combination of the mother liquor with the rinse solution the mixture was checked for residual product and discarded. The filter cake was dried in a flow of dry nitrogen at ambient temperature for 2 hrs. until LOD=65% wt.

The crude product urolithin A was received in a yield of 46.6 kg and was used in batch RR03L111A0 as it was.

Batch RR02L111A0.

The reactor was charged with 8-methyl urolithin A (15.25 kg, 63.0 mol), 5.0 equiv. of aluminum chloride (42.0 kg, 315.0 mol) and 10.3 vol. of toluene (137.0 kg, 157 L). Agitation was started and the reaction mixture was heated to 90° C. within 72 min. Stirring was continued for 2 hours at 90-96° C. After cooling the reaction mass to 58° C. over 30 min, 0.7 vol. of water for injection (10.2 L) followed by 10.5 vol. of purified water (160 L) were added within 2 hours carefully at 51-58° C. Agitation was continued for 2 hours at 39-51° C. to remove all tipping from the reactor wall before the mixture was cooled to 37° C. in 5 min. The product was collected by filtration at 30-37° C. (35 min required) and the filter cake was rinsed with 4.2 vol. of methanol (50.0 kg, 63 L, 20 min required). After combination of the mother liquor with the rinse solution the mixture was checked for residual product and discarded. The filter cake was dried in a flow of dry nitrogen at ambient temperature for 2 hrs. until LOD=55% wt.

The crude product urolithin A was received in a yield of 43.8 kg and was used in batch RR03L111A0 as it was.

Batch RR03L111A0.

The reactor was charged with urolithin A from previous batches RR01L111A0 (45.6 kg (LOD: 65% wt.)), RR02L111A0 (43.3 kg (LOD: 55% wt.)) and 4.1 vol. of DMSO (139 kg, 126 L). Agitation was started and stirring was continued until a clear solution was obtained at 20-25° C. (1.5 hours). A second reactor was charged with 12.1 vol. of purified water (370 L) and agitation was initiated. The DMSO-solution was added through a particle filter over 65 min at 20-24° C. The line (1$^{st}$ reactor, particle filter, 2$^{nd}$ reactor) was rinsed with 0.3 vol. of DMSO (10 kg, 9 L) and the rinse solution was combined with the suspension in the second reactor. Stirring of the suspension was continued for 35 min at 23° C. The raw product was collected by filtration at ambient temperature (7 days required) and the filter cake was rinsed with 4.1 vol. of purified water (125 L, 3.5 days required). After combination of the mother liquor with the rinse solution the mixture was checked for residual product and disposed. The filter cake was dried in a flow of dry nitrogen at ambient temperature for 7 hours until LOD=86-89% wt. Drying of the filter cake was continued under reduced pressure for 18 hours at max. 60° C. until LOD=81-86% wt.

The raw product urolithin A was obtained in a yield of 25.2 kg and was used in batch RR03L111A1 as it was.

Batch RR03L111A1.

The reactor was charged with urolithin A from previous batch RR03L111A0 (25.2 kg) and 8.2 vol. of particle free acetic acid (264 kg, 251 L). Agitation was started and the slurry was heated to reflux within 65 min. Reflux was continued for 5 hours before cooling to 41° C. within 50 min. The solid was collected by filtration at 20-26° C. (25 hours required) and the filter cake was rinsed subsequently with 4.1 vol. of particle free acetic acid (132 kg, 126 L, 21 hours required) and 4.1 vol. of particle free TBME (93 kg, 126 L, 16 hours required). After combination of the mother liquor with the rinse solution the mixture was checked for residual product and discarded. The filter cake was dried under reduced pressure at 80° C. for 21 hours. The damp product was delumped and drying was continued under reduced pressure for 33 hours at 20-80° C.

The product urolithin A was obtained in 24.1 kg corresponding to an overall yield of 84% for the ether cleavage and 96% recovery for the re-processing.

TABLE 13

Analytical results for urolithin A from GMP-batch RR03L111A1 and PLPD experiments

| Test | Specification | RR03L111A1 | PLPD experiments |
|---|---|---|---|
| Appearance | off-white to beige solid | beige solid | pale yellow to yellow solid |
| Identity by FT-IR | conforms to reference | conforms | n.a. |
| Assay by HPLC | report result | 97.0% wt. | 97-98% wt. |
| Purity by HPLC | >97 area % | 99.67% | 99.7-99.9% |
| Water by Karl Fischer | report result | 0.14% wt. | n.a. |
| Residual Solvents | | | |
| Toluene | max. 890 ppm | 185 ppm | 0-9 ppm |
| Methanol | max. 3000 ppm | n.d. | n.d. |
| TBME | max. 5000 ppm | n.d. | 0-18 ppm |
| Acetic Acid | max. 5000 ppm | 1271 ppm | 1341-1854 ppm |
| DMSO | max. 5000 ppm | 414 ppm | 55-73 ppm |
| ROI | report result | <0.1% wt. | n.a. |
| Heavy Metals | max. 20 ppm | <20 ppm | n.a. |
| Copper | report result | <1 ppm | <1 ppm |
| Aluminum | report result | 21 ppm | 6-17 ppm |

TABLE 14

Key raw materials for the purification of urolithin A in batches RR01L111A0/RR02L111A0

| Compound | CAS-No. | Purity[a] | Lot-No. |
|---|---|---|---|
| 8-methyl UA | | 99.5% | RR01L108A0 |
| Aluminium Chloride | 7446-70-0 | 99.6% | C13077113 |
| Toluene | 108-88-3 | 99.97% | 491629 |
| Purified Water | 7732-18-5 | n.a. | 0406130715 |
| Methanol | 67-56-1 | 99.9% | PA108058 |
| Water for Injection | 7732-18-5 | n.a. | 14DE6058 |

TABLE 15

Key raw materials for the purification of urolithin A in batch RR03L111A0

| Compound | CAS-No. | Purity[a] | Lot-No. |
|---|---|---|---|
| Purified Water | 7732-18-5 | n. a. | 0506130715 |
| Urolithin A | — | 95.9% | RR01L111A0 |
| | | 96.8% | RR02L111A0 |
| DMSO | 7732-18-5 | 99.91% | PC10062 |
| Acetic Acid | 64-19-7 | 99.9% | 254749 |
| TBME | 1634-04-4 | 100.0% | 500106 |

TABLE 16

Key raw materials for the purification of urolithin A in batch RR03L111A1

| Compound | CAS-No. | Purity[a] | Lot-No. |
|---|---|---|---|
| Urolithin A | — | n.d. | RR03L111A0 |
| Acetic Acid | 64-19-7 | 99.9% | 510499 |
| TBME | 1634-04-4 | 100.0% | 500106 |

[a]According to CoA or other analytical information.

TABLE 17

Yields of the manufacturing campaign

| Starting material | Input | Product [kg] | Output [kg] | Yield [%][a] | Comment |
|---|---|---|---|---|---|
| 2-Bromo-5-methoxy benzoic acid | 40.00 | 8-methyl UA | 31.28 | 75 | batch separated in two portions for subsequent step |
| 8-methyl UA | 15.25 | Urolithin A | 46.58 | [b] | 1st batch: ether cleavage |
| 8-methyl UA | 15.25 | Urolithin A | 43.78 | [b] | 2nd batch: ether cleavage |
| Urolithin A | 45.6 + 43.2 | Urolithin A | 25.22 | 88 | combined polish filtration of 1st and 2nd batch |
| Urolithin A | 25.18 | Urolithin A | 24.14 | 96 | re-processing of urolithin A |
| | | overall yield: 63% | | | |

[a]yield "as is" (no correction for assay)
[b]no yield given here: damp filter cakes used for combined polish-filtration.

EQUIVALENTS

The invention has been described broadly and generically herein. Those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention. Further, each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

What is claimed is:

1. A method of preparing a compound of formula I, comprising the step of combining in an aqueous alkaline solvent mixture a copper-containing catalyst, a compound of formula II, and a compound of formula III, thereby forming the compound of formula I;

wherein the compound of formula I is represented by:

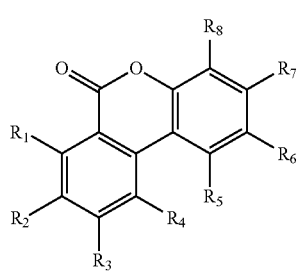

(I)

$R_1$, $R_2$, $R_3$, $R_4$, $R_5$, $R_6$, $R_7$, and $R_8$ are, independently for each occurrence, selected from the group consisting of H and OR;

wherein, if two OR are present at adjacent positions, then the two R groups taken together may represent a methylene (—$CH_2$—) group;

R is selected from the group consisting of H and lower alkyl;

the compound of formula II is represented by:

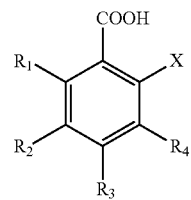

(II)

or an alkyl or aryl ester thereof; wherein X is selected from the group consisting of Cl, Br, and I; and the compound of formula III is represented by:

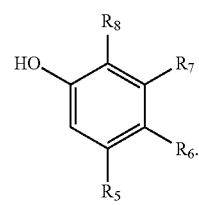

(III)

2. The method of claim 1, wherein the copper-containing catalyst is selected from the group consisting of copper powder, copper-bronze couple, $CuSO_4$ hydrate, anhydrous $CuSO_4$, $Cu(acac)_2$, CuCl, $CuCl_2$, CuBr, $CuBr_2$, CuI, $Cu_2O$, CuO, CuOTf, CuCN, and mixtures thereof.

3. The method of claim 1, wherein the copper-containing catalyst is $CuSO_4$ hydrate or anhydrous $CuSO_4$.

4. The method of claim 1, wherein the amount of copper-containing catalyst is at least a trace amount but less than 0.01 equivalents relative to either formula II or formula III.

5. The method of claim 1, wherein the aqueous alkaline solvent comprises LiOH, NaOH, KOH, CsOH, $Na_2CO_3$, $CaCO_3$, or $Cs_2CO_3$.

6. The method of claim 1, wherein the aqueous alkaline solvent comprises NaOH or KOH.

7. The method according to claim 1, wherein the yield of formula I is at least about 40% relative to the limiting reagent between formula II and formula III.

8. The method of claim 1, wherein formula I contains less than about 1 ppm copper.

9. The method of claim 1, wherein X is Cl.

10. The method of claim 1, wherein X is Br.

11. The method of claim 1, wherein $R_2$ is H or OMe.

12. The method of claim 1, wherein $R_1$, $R_4$, $R_5$, $R_6$, and $R_8$ are each H.

13. The method of claim 1, wherein $R_2$ is OMe; and $R_3$, $R_7$, and $R_8$ are each OH or OMe.

14. The method of claim 1, wherein $R_1$, $R_3$, $R_4$, $R_5$, $R_6$, and $R_8$ are each H; $R_2$ is OMe; and $R_7$ is OH;

$R_1$, $R_3$, $R_4$, $R_5$, $R_6$, $R_7$, and $R_8$ are each H; and $R_2$ is OMe;

$R_1$, $R_4$, $R_5$, $R_6$, and $R_8$ are each H; $R_2$ is OMe; and $R_3$ and $R_7$ are each OH; or $R_1$, $R_4$, $R_5$, and $R_6$ are each H; $R_2$ is OMe; and $R_3$, $R_7$, and $R_8$ are each OH.

15. The method of claim 1, wherein $R_1$, $R_3$, $R_4$, $R_5$, $R_6$, and $R_8$ are H; $R_2$ is OMe; and $R_7$ is OH.

16. The method of claim 1, wherein $R_1$, $R_2$, $R_3$, $R_4$, $R_5$, $R_6$, and $R_8$ are H; and $R_7$ is OH.

* * * * *